United States Patent
Li et al.

(10) Patent No.: US 10,654,895 B2
(45) Date of Patent: May 19, 2020

(54) POLYPEPTIDE, DNA MOLECULE ENCODING THE POLYPEPTIDE, VECTOR, PREPARATION METHOD AND USE

(71) Applicant: WUHAN MORE BIOTECHNOLOGY CO., LTD., Hubei (CN)

(72) Inventors: Wenxin Li, Hubei (CN); Zhijian Cao, Hubei (CN); Yingliang Wu, Hubei (CN); Zesheng Wang, Hubei (CN); Song Han, Hubei (CN)

(73) Assignee: WUHAN MORE BIOTECHNOLOGY CO., LTD., Hubei (CN)

( * ) Notice: Subject to any disclaimer, the term of this patent is extended or adjusted under 35 U.S.C. 154(b) by 0 days.

(21) Appl. No.: 16/178,499

(22) Filed: Nov. 1, 2018

(65) Prior Publication Data

US 2019/0055287 A1 Feb. 21, 2019

Related U.S. Application Data

(62) Division of application No. 14/904,674, filed as application No. PCT/CN2014/082341 on Jul. 16, 2014, now abandoned.

(30) Foreign Application Priority Data

Jul. 17, 2013 (CN) .......................... 2013 1 0300278
Jul. 10, 2014 (CN) .......................... 2014 1 0327573

(51) Int. Cl.
| | | |
|---|---|---|
| C07K 7/08 | (2006.01) | |
| A61K 38/08 | (2019.01) | |
| A61K 38/10 | (2006.01) | |
| C07K 7/06 | (2006.01) | |
| C12N 15/63 | (2006.01) | |
| A61K 38/00 | (2006.01) | |

(52) U.S. Cl.
CPC ............... *C07K 7/08* (2013.01); *A61K 38/08* (2013.01); *A61K 38/10* (2013.01); *C07K 7/06* (2013.01); *C12N 15/63* (2013.01); *A61K 38/00* (2013.01); *Y02A 50/473* (2018.01); *Y02A 50/475* (2018.01); *Y02A 50/481* (2018.01); *Y02A 50/483* (2018.01)

(58) Field of Classification Search
CPC .................................. C07K 7/08; A61K 38/08
See application file for complete search history.

(56) References Cited

U.S. PATENT DOCUMENTS

| | | | |
|---|---|---|---|
| 6,235,278 B1 | 5/2001 | Miller | |
| 6,703,491 B1 | 3/2004 | Homburger | |
| 6,783,961 B1 | 8/2004 | Edwards | |
| 7,090,973 B1 | 8/2006 | Breton | |
| 7,214,786 B2 | 5/2007 | Kovalic | |
| 7,244,584 B2 | 7/2007 | Zuker | |
| 7,745,391 B2 | 6/2010 | Mintz | |
| 7,842,467 B1 | 11/2010 | Heidbrink | |
| 8,067,671 B2 | 11/2011 | Boukharov | |
| 9,012,723 B2 | 4/2015 | Guo | |
| 2007/0192889 A1 | 8/2007 | La Rosa | |
| 2010/0261653 A1 | 10/2010 | Krasnoperov | |
| 2017/0037426 A1 | 2/2017 | Alexandrov | |

FOREIGN PATENT DOCUMENTS

| | | | |
|---|---|---|---|
| CN | 101063102 | * 4/2007 | ............ A61K 38/17 |
| CN | 101063102 A | 10/2007 | |
| CN | 101063103 A | 10/2007 | |
| CN | 101450966 A | 6/2009 | |
| CN | 101775068 A | 7/2010 | |
| CN | 101284870 B | 9/2011 | |
| CN | 102295683 A | 12/2011 | |
| CN | 102382839 A | 3/2012 | |
| CN | 102516365 A | 6/2012 | |
| CN | 103360464 A | 10/2013 | |
| WO | WO2013/040142 A2 | 3/2013 | |

OTHER PUBLICATIONS

Fan et al., 2011, Ctriporin, a New Anti-Methicillin-Resistant *Staphylococcus aureus* Peptide from the Venom of the Scorpion *Cherilus tricostatus*, Antimicrobial Agents and Chemotherapy, 55(11): 5220-5229.*
International Search Report for Application No. PCT/CN2014/082341, dated Oct. 8, 2014.
European Search Report for EP Application No. 14827050.7, dated Feb. 8, 2017.
Zhengyang Zeng et al., "A Scorpion Defensin BmKDfsin4 Inhibits Hepatitis B Virus Replication in Vitro," TOXINS, vol. 8, No. 5, May 2016 (May 2016).
Office Action dated Sep. 3, 2018 in Chinese Patent Application No. 201410327573.5 with English Summary, 10 pages.

(Continued)

*Primary Examiner* — Amber D Steele
(74) *Attorney, Agent, or Firm* — Squire Patton Boggs (US) LLP

(57) ABSTRACT

A polypeptide, a DNA molecule encoding the polypeptide, a vector, a preparation method and a use therefor are disclosed. The polypeptide comprises an amino acid sequence represented by formula (I) or formula (II): formula (I) comprises an amino acid sequence represented by SEQ ID NO: 1; formula (II) comprises an amino acid sequence obtained by subjecting the amino acid sequence represented by SEQ ID NO: 1 to modification, substituted, and deletion or addition of one or more amino acids. The polypeptide may be used in the preparation of drugs that treat or prevent diseases related to infections caused by bacteria, and can also be used in the preparation of drugs that promote tissue repair and wound healing.

6 Claims, 2 Drawing Sheets

Specification includes a Sequence Listing.

(56) References Cited

OTHER PUBLICATIONS

Zeng et al., 2001, Precursor of a Novel Scorpion Venom Peptide (BmKn1) with no Disulfide Bridge from Buthus martensii Karsch, IUBMB Life, 51: 117-120.

Ma et al., 2011, Extreme diversity of scorpion venom peptides and proteins revealed by transcriptomic analysis: Implication for proteome evolution of scorpion venom arsenal, Journal of Proteomics, 75: 1563-1576.

\* cited by examiner ttcctctgtgaaagtaagttctgtgaaactcactcttcgataaaatgaaatctcagaccttttccttcttttctagttgt
tttattattagcaatttcacaatcagaagctttatcaggatcgccaggctcctcaggatctttggaaaaagaagtat
gagagatatggatactatgaaatacttatatgaaccaagtttgagtgcagctgacttgaaaaccttacaaaaacta
atggaaaattactgattatttgaatataataatgttatctctattttagattataaatatttcttttgaaaaaaaaaaaaaa
aaaaaaa

Figure 1

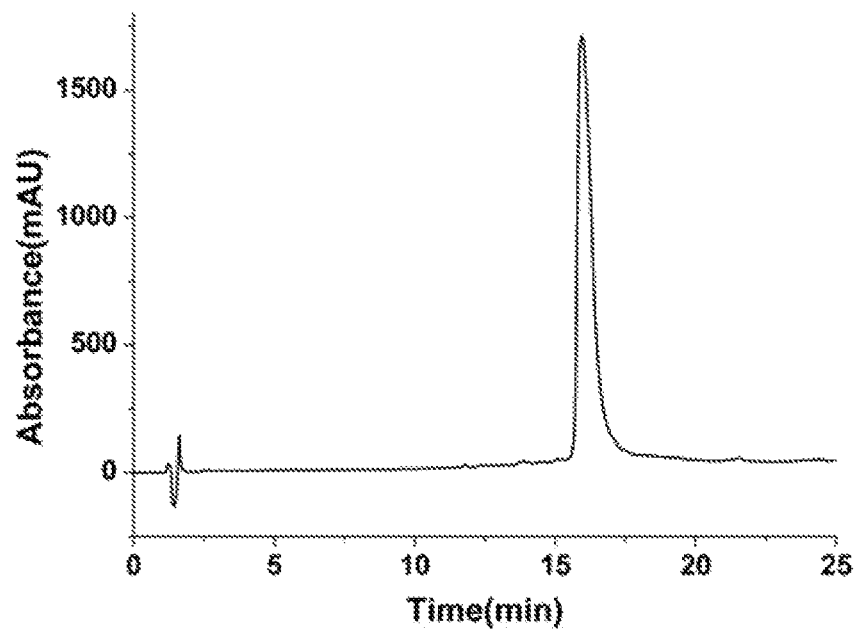

Figure 2

POLYPEPTIDE, DNA MOLECULE ENCODING THE POLYPEPTIDE, VECTOR, PREPARATION METHOD AND USE

This application is a divisional application of U.S. application Ser. No. 14/904,674 filed Jan. 12, 2016, which is a national phase application of PCT/CN2014/082341 filed Jul. 16, 2014, which claims the priorities of Chinese Patent Application No. 201310300278.6, entitled "POLYPEPTIDE, DNA MOLECULE ENCODING THE POLYPEPTIDE, VECTOR, PREPARATION METHOD AND USE" filed with the Chinese State Intellectual Property Office on Jul. 17, 2013, and Chinese Patent Application No. 201410327573.5, entitled "POLYPEPTIDE, DNA MOLECULE ENCODING THE POLYPEPTIDE, VECTOR, PREPARATION METHOD AND USE" filed with the Chinese State Intellectual Property Office on Jul. 10, 2014, which are both incorporated herein by reference in their entirety.

FIELD OF THE INVENTION

The present invention relates to the field of biotechnology, particularly to a polypeptide, DNA molecule encoding the polypeptide, vector, preparation method and use.

BACKGROUND OF THE INVENTION

Among various wounds, no matter in the clinical treatment of various injuries such as burn injury, cold injury, crush injury, war injury, animal bite, nuclear radiation injury and combined injury, or in the open or closed wound, the prevention of infections, the promotion of tissue repair and the wound healing are always an everlasting subject matter in the treatment of wound.

Bacterial infections are cute systemic infections or local infections caused by pathogenic bacteria or opportunistic pathogenic bacteria invading the blood circulation or local environment for growth and propagation therein and producing toxins or other metabolites, which is clinically characterized by chills, hyperpyrexia, erythra, joint pain and hepatosplenomegaly, partly with infectious shock and migrated lesions. Especially in elders, children, persons with a chronic disease or immunodeficiency, or in persons with complications due to delayed treatment, the condition may develop to septicemia or septicopyemia.

There are various kinds of pathogenic bacteria or opportunistic pathogenic bacteria capable of infecting human, which can invade the tissues and organs in different sites in human, causing local or systemic inflammatory responses and various diseases.

In nonspecific infections (i.e., the pyogenic infections), common ones are furuncle, carbuncle, erysipelas, acute lymphangitis, acute lymphadenitis, paronychia, felon, lateral pyogenic tenosynovitis of fingers, bursitis, palm deep space infection, pyemia, bacteremia and others, caused by pathogenic bacteria such as *Staphylococcus aureus, Streptococcus hemolyticus, Escherichia coli, Pseudomonas aeruginosa* and the like. The infection may be caused by a single bacterium, or the infection may be a combined infection caused by several bacteria, and thus, it is important to have a broad spectrum for a clinic medicament.

Acne is also a nonspecific infection commonly and frequently occurred in adolescents, which sometimes occurs in middle-aged people. Clinical manifestations thereof include whitehead acne, blackhead acne, inflammatory papule, secondary abscess, hydatoncus or nodule, paining and itching. If infection happens, there may leave scars, influencing the appearance as well as physical and psychological health. Now, it is known that there are many pathogenic factors and segments playing a key role in the onset, progression and turnover of acne, among which the most important reason is microbial action in hair follicle and pilosebaceous units, wherein the first cause is anaerobic *Propionibacterium acnes*, and the second cause is aerobic *Staphylococcus epidermidis* and *Staphylococcus aureu*. Bacterial infection is an important pathogenic factor in the onset of acne.

A specific infection refers to tuberculosis, tetanus, gas gangrene, anthrax, pertussis, epidemic encephalomyelitis, gonorrhea, typhia, bacillary dysentery, diphtheria, each of which is an disease specifically caused by *Mycobacterium tuberculosis, Clostridium tetani, Clostridium perfringens, Bacillus anthraci, Bordetella pertussis, Neisseria meningitides, Neisseria gonorrhoeae, Salmonella typhi, Shigella, Corynebacterium diphtheria*, respectively. A specific infection is different from a general infection in terms of pathogenic bacteria, disease progression and treatment, etc., which are the main subjects in epidemiological studies.

Promotion of wound healing is one of the two problems in traumatology, which is equally as important as anti-infection. Recently, with the intervention of modern cell biology and molecular biology studies, cell activities and influence factors thereof during would healing have been observed in a large number of experiments, and it was considered that various growth factors were involved in the regulation of the wound healing process, with the possible mechanisms being very complex.

A chronic refractory infection wound surface is a general term for wound surfaces infected with bacteria in a chronic refractory wound on the body surface. The chronic refractory wound surface on the body surface is caused by a series of wounds and diseases. The wound surfaces which are developed on the body surface and do not heal for a long time mainly include traumatic ulcers, lower extremity venous ulcers, pressure ulcers and diabetic ulcers. Due to features such as development on the body surface, long course of disease, large influences on appearance, high incidence of complications and extremely high treatment expenses, there will be large influences on lives and qualities of patients, which is an important issue that modern society must face.

Among the chronic refractory wound surfaces on the body surface, 87% suffer from bacterial infections, mainly with *Staphylococcus aureus, Pseudomonas aeruginosa* and *Escherichia coli*. Due to the long treatment course, a large majority of the bacteria on the wound surface would develop drug resistance in varying degrees; particularly when the refractory wound surface is infected with MRSA, MRCNS, erythromycin-resistant *Streptococcus pyogenes*, ESBL-producing *Escherichia coli*, imipenem-resistant *Pseudomonas aeruginosa* strains (IPM-R strains). Due to the lack of clinically effective medicaments for treatment, the serious consequences of amputation may happen.

Eczema is a skin inflammatory response having polymorphic skin damages and tendency of exudation, which is caused by various endogenous and exogenous factors, the etiology is unresolved and is believed to be multifactorial The subjective symptom is fierce pruritus. Recurrence risk is high and is accompanied by secondary bacterial infections, which cannot be cured for many years.

Regarding prevention of wound infections, a common drug is antibiotics; however, drug resistance of a pathogenic bacterium caused by antibiotics abuse has made no drug available for many wounds, resulting in systemic infections in patients: pyemia, bacteremia, serious injuries in other organs, or chronic refractory wound surfaces forming on the body surface. The drug resistance issue of antibiotics has become a global focus. Another hazard of the drug-resistance bacteria is that they can spread among populations between different regions or counties. *Streptococcus pneumonia* is a common etiological bacterium causing bacterial pneumonia. Recently, the drug resistance thereof to antibiotics has been on the rise, and there have been multi-drug resistant strains developed, which has become a troublesome problem in clinical infection control. Currently, many antibacterial infection drugs, mostly, have poor efficacy due to infections with drug-resistant bacteria, in particular methicillin-resistant *Staphylococcus aureus* (MRSA). Therefore, there is an urgent need to develop a new antiseptic substance.

Recently, studies on bioactive antiseptic peptides have become frontier science in antibiotics development in international pharmacies. There have been over 1300 antiseptic peptides successfully separated and identified currently, which were commonly characterized by a small molecular weight (12-100 amino acid residues), cationic polymer and amphiphilic construction. These bioactive substances referred to as peptide antibiotics, due to features such as pure living organism, strong stability and antiseptic ability, broad spectrum, no drug resistance, no toxic side effect and "three-induced" action, have been considered as optimal alternatives to the existing antibiotics. An active antiseptic active Ctryamp polypeptide or structurally homologous polypeptides thereof are naturally occurring antiseptic peptides molecules obtained from *Chaerilus tryznai* Kovarik. They can rapidly kill microorganisms (including drug-resistant bacteria produced by using traditional antibiotics) without producing drug resistance by itself, with different production mechanism, bactericidal mechanism and mode of action from traditional antibiotics, and from which the hydrolyzed amino acids may facilitate the generation of skin tissues.

SUMMARY OF THE INVENTION

In view of this, the present invention provides a polypeptide, DNA molecule encoding the polypeptide, vector, preparation method and use. This antiseptic active polypeptide from *Chaerilus tryznai* Kovarik has a broad-spectrum and potent inhibitory effect on gram-positive bacteria, gram-negative bacteria, anaerobic bacterium and clinically drug-resistant pathogenic bacteria. It can promote both tissue repair and wound healing, and is thus useful for the manufacture of a medicament for the treatment or prevention of diseases associated with nonspecific infections, specific infections caused by bacteria, anaerobic bacterium, in particular drug-resistant bacteria, as well as a medicament for promoting tissue repair and wound healing. The additives (such as additives of cosmetics, health products, feeds and others) as provided in the present invention containing the broad-spectrum antiseptic active polypeptide as effective ingredient can prevent the bacterial infections and promote the tissue repair. Thus, they are useful for the prevention of bacterial infections and promotion of tissue repair, resulting in a good prevention for bacterial infections and good promotion of skin tissue repair without any side effect.

In order to achieve the above objects of the present invention, the present invention provides the following technical solutions.

The present invention provides a polypeptide having any one of the amino acid sequences as set forth in (I) and (II):

(I) the amino acid sequence as set forth in SEQ ID NO: 1;

(II) amino acid sequences obtained from the amino acid sequence as set forth in SEQ ID NO: 1 with modification, substitution, deletion or addition of one or more amino acids.

The present invention discloses a group of structurally homologous polypeptides of a Ctryamp polypeptide from *Chaerilus tryznai* Kovarik, of which the amino acid sequence is as set forth in SEQ ID NO: 1. Based on the mature peptide sequence (FIRIARLLRIF (SEQ ID NO: 2)) of Ctryamp, its secondary structure was predicted by using on-line NPS@ server [DSC method (Discrimination of protein Secondary structure Class)]. Its secondary structure was shown as a diagram by using the software AHTHEP-ROT 2000. Results showed that, the Ctryamp contained 100% of α-Helix structure, had a typical amphiphilic α-Helix structure and comprised a large number of basic residues (Arg) with net positive charges. According to the helix diagram of the polypeptide sequence and by large numbers of point mutations on the polypeptide sequence FIRIARLL-RIF (SEQ ID NO: 2) of Ctryamp, it is found that the sequence $FIX_1IAX_2LLX_3IF$ ($X_1$, $X_2$ and $X_3$ are any one of three basic amino acids His, Arg and Lys) (SEQ ID NO: 1) does not influence the amphiphilicity features thereof (Table 1). Therefore, the present invention provides a group of structurally homologous polypeptides (SEQ ID NO: 1) of a Ctryamp polypeptide from *Chaerilus tryznai* Kovarik.

In some embodiments of the present invention, the modification includes amidation, phosphorylation, methylation, acetylation, ubiquitination, glycosylation or carbonylation.

In other embodiments of the present invention, the modification is acetylation;

specifically, a polypeptide produced with the modification has the amino acid sequence as set forth in SEQ ID NO: 52.

Preferably, the substitution is substitution with 1, 2, 3, 4 or 5 amino acids.

When substituted by one amino acid, the polypeptide does not have the amino acid sequence as set forth in SEQ ID NO: 21.

More preferably, a polypeptide produced with the substitution has any one of the following amino acid sequences:
the amino acid sequence as set forth in SEQ ID NO: 22;
the amino acid sequence as set forth in SEQ ID NO: 23;
the amino acid sequence as set forth in SEQ ID NO: 24;
the amino acid sequence as set forth in SEQ ID NO: 25;
the amino acid sequence as set forth in SEQ ID NO: 26;
the amino acid sequence as set forth in SEQ ID NO: 27.

Preferably, the deletion is deletion of 1, 2, 3, 4 or 5 amino acids. More preferably, the deletion is deletion of 1 or 2 amino acids. Further preferably, when the deletion is of 1 amino acid, the deleted amino acid residue is not at position 4 or 9.

More preferably, a polypeptide produced with the deletion has any one of the following amino acid sequences:
the amino acid sequence as set forth in SEQ ID NO: 28;
the amino acid sequence as set forth in SEQ ID NO: 29;
the amino acid sequence as set forth in SEQ ID NO: 32.

Preferably, the addition is addition of 1, 2, 3, 4, 5, 6, 7, 8, 9 or 10 amino acids. When the addition is addition at the N terminal of the polypeptide having the amino acid sequence as set forth in SEQ ID NO: 1, addition of 1, 2, 3, 4 or 5 amino acids is preferred.

More preferably, a polypeptide produced with the addition has any one of the following amino acid sequences:
the amino acid sequence as set forth in SEQ ID NO: 36;
the amino acid sequence as set forth in SEQ ID NO: 37;

the amino acid sequence as set forth in SEQ ID NO: 38;
the amino acid sequence as set forth in SEQ ID NO: 39;
the amino acid sequence as set forth in SEQ ID NO: 40;
the amino acid sequence as set forth in SEQ ID NO: 41;
the amino acid sequence as set forth in SEQ ID NO: 42;
the amino acid sequence as set forth in SEQ ID NO: 43;
the amino acid sequence as set forth in SEQ ID NO: 44;
the amino acid sequence as set forth in SEQ ID NO: 45.

Preferably, it does not have the amino acid sequence as set forth in SEQ ID NO: 4, SEQ ID NO: 5, SEQ ID NO: 6, or SEQ ID NO: 53 or SEQ ID NO: 54.

Preferably, the polypeptide provided in the present invention has an amino aide sequence as set forth in any one of SEQ ID NO: 2, SEQ ID NOs: 7 to 20, SEQ ID NOs: 22 to 29, SEQ ID NO: 32, SEQ ID NOs: 36 to 45 or SEQ ID NO: 52.

The present invention specifically discloses a Ctryamp polypeptide from *Chaerilus tryznai* Kovarik, which has the amino acid sequence as set forth in SEQ ID NO: 2. A precursor organizational form of the Ctryamp encodes 68 amino acid residues consisting of three portions, that is, a signal peptide (23 residues), mature peptide (11 residues) and precursor peptide (34 residues). As shown in FIG. 1, below the cDNA sequence is the deduced corresponding amino acid sequence; amino acids in the signal peptide are labeled in italic; amino acids in the mature peptide are amino acid in the shadowed area; and the underlined amino acids are for the precursor peptide of the C terminal. Therefore, the present invention provides an antiseptic peptide from *Chaerilus tryznai* Kovarik: FIRIARLLRIF (SEQ ID NO: 2).

The present invention further provides the use of the polypeptide for the manufacture of an antiseptic agent. The polypeptide has any one of the amino acid sequences as set forth in (I) and (II):

(I) the amino acid sequence as set forth in SEQ ID NO: 1;

(II) the amino acid sequence obtained from the amino acid sequence as set forth in SEQ ID NO: 1 with modification, substitution, deletion or addition of one or more amino acids;

wherein the modification includes amidation, phosphorylation, methylation, acetylation, ubiquitination, glycosylation or carbonylation; the substitution is substitution of 1, 2, 3, 4 or 5 amino acids; the deletion is deletion of 1, 2, 3, 4 or 5 amino acids; the addition is addition of 1, 2, 3, 4, 5, 6, 7, 8, 9 or 10 amino acids; and the polypeptide does not have the amino acid sequence as set forth in SEQ ID NO: 4, SEQ ID NO: 5, SEQ ID NO: 6, SEQ ID NO: 53 or SEQ ID NO: 54. Preferably, the polypeptide has the amino acid sequence as set forth in SEQ ID NO: 2.

In some embodiments of the present invention, the antiseptic agent is useful in inhibiting a bacterium.

In some embodiments of the present invention, the bacterium is a gram-positive bacterium and/or gram-negative bacterium.

The antiseptic results showed that, the synthetic Ctryamp polypeptide and structurally homologous polypeptides thereof had potent inhibitory effect on the growth of a standard gram-negative bacterium *Escherichia coli* CCTC-CAB94012 and gram-positive bacterium *Staphylococcus aureus* CCTCCAB94004. At 6.25 µg/mL, the Ctryamp polypeptide and structurally homologous polypeptides thereof have an inhibition rate of 100% on the *Escherichia coli* CCTCCAB94012; while at 6.25 µg/mL, also have an inhibition rate of 100% on the *Staphylococcus aureus* CCTCCAB94004 (Table 2). It showed that the Ctryamp polypeptide had potent inhibitory effect on the proliferation of gram-negative bacteria, in particular, pathogenic *Escherichia coli* and *Pseudomonas aeruginosa* (Table 3), in which the Ctryamp polypeptide had a minimal inhibitory concentration of 8-16 µg/mL on *Pseudomonas aeruginosa*. The antiseptic results also showed that, the Ctryamp polypeptide had potent inhibitory effect on the proliferation of gram-positive bacterium bacteria and the growth of anaerobic bacterium bacteria (Table 3).

In some embodiments of the present invention, the gram-positive bacteria belong to *Staphylococcus, Streptococcus, Enterococcus, Mycobacterium,* anaerobic bacterium or *Corynebacterium*. The antiseptic results showed that, the synthetic Ctryamp polypeptide had potent inhibitory effect on clinically drug-resistant bacteria (methicillin-resistant *Staphylococcus aureus*, methicillin-resistant coagulase-negative staphylococci, erythromycin-resistant *Streptococcus pyogenes*, ESBL-producing *Escherichia coli* resistant to penicillin and cephalosporins, to monoamides, having cross drug-resistance to quinolones, aminoglycosides, sulfonamides, and imipenem-resistant *Pseudomonas aeruginosa* (IPM-R strain)) (Table 3).

The antiseptic results showed that, the chemically synthetic Ctryamp polypeptide had potent inhibitory effect on bacteria causing specific infections (including *Bordetella pertussis, Clostridium tetani, Clostridium perfringens, Shigella, Salmonella typhi* and *Corynebacterium diphtheria*) (Table 3).

In other embodiments of the present invention, the gram-negative bacterium belongs to *Neisseria, Enterobacteriaceae, Pseudomonas, Acinetobacter, Bordetella* or *Haemophilus*.

The present invention further provides the use of the polypeptide for the manufacture of a medicament for the prevention and/or treatment of bacterial infection disease and/or eczema. The polypeptide has any one of the amino acid sequences as set forth in (I) and (II):

(I) the amino acid sequence as set forth in SEQ ID NO: 1; (II) amino acid sequences obtained from the amino acid sequence as set forth in SEQ ID NO: 1 with modification, substitution, deletion or addition of one or more amino acids;

wherein the modification includes amidation, phosphorylation, methylation, acetylation, ubiquitination, glycosylation or carbonylation; the substitution is substitution of 1, 2, 3, 4 or 5 amino acids; the deletion is deletion of 1, 2, 3, 4 or 5 amino acids; the addition is addition of 1, 2, 3, 4, 5, 6, 7, 8, 9 or 10 amino acids; and the polypeptide does not have the amino acid sequence as set forth in SEQ ID NO: 4, SEQ ID NO: 5, SEQ ID NO: 6, SEQ ID NO: 53 or SEQ ID NO: 54. Preferably, the polypeptide has the amino acid sequence as set forth in SEQ ID NO: 2.

In some embodiments of the present invention, the bacterium in the use of the polypeptide for the manufacture of a medicament for the prevention and/or treatment of a bacterial infection disease and/or eczema is a gram-positive bacterium and/or gram-negative bacterium.

In some embodiments of the present invention, the gram-positive bacterium in the use of the polypeptide for the manufacture of a medicament for the prevention and/or treatment of a bacterial infection disease and/or eczema belongs to *Staphylococcus, Streptococcus, Enterococcus, Mycobacterium,* anaerobic bacterium or *Corynebacterium*.

In other embodiments of the present invention, the gram-negative bacterium in the use of the polypeptide for the manufacture of a medicament for the prevention and/or treatment of a bacterial infection disease and/or eczema belongs to *Neisseria, Enterobacteriaceae, Pseudomonas, Acinetobacter, Bordetella* or *Haemophilus*.

In some embodiments of the present invention, the infection in the use of the polypeptide for the manufacture of a medicament for the prevention and/or treatment of a bacterial infection disease and/or eczema is a nonspecific infection and/or specific infection.

In some embodiments of the present invention, the nonspecific infection in the use of the polypeptide for the manufacture of a medicament for the prevention and/or treatment of a bacterial infection disease and/or eczema is furuncle, carbuncle, erysipelas, acute lymphangitis, acute lymphadenitis, paronychia, felon, lateral pyogenic tenosynovitis of fingers, bursitis, palm deep space infection, pyemia or bacteremia.

In some embodiments of the present invention, the specific infection in the use of the polypeptide for the manufacture of a medicament for the prevention and/or treatment of a bacterial infection disease and/or eczema is tuberculosis, tetanus, gas gangrene, anthrax, pertussis, epidemic encephalomyelitis, gonorrhea, typhia, bacillary dysentery or diphtheria.

In some embodiments of the present invention, the infection is an infection caused by MRSA, MRCNS, erythromycin-resistant *Streptococcus pyogenes*, ESBL-producing *Escherichia coli* or imipenem-resistant *Pseudomonas aeruginosa* (IPM-R strain).

In other embodiments of the present invention, the infection is a local infection, systemic infection or toxic disease caused by *Staphylococcus aureus*.

In other embodiments of the present invention, the infection is a urinary system infection, septicemia or postoperative infection, caused by coagulase-negative staphylococci.

In other embodiments of the present invention, the infection is a pyogenic inflammation, rheumatic fever and acute glomerulonephritis, scarlatina, bacterial pneumonia, saprodontia, subacute bacterial endocarditis or newborn infection, caused by *Streptococcus*.

In other embodiments of the present invention, the infection is lobar pneumonia, trachitis, otitis media, meningitis, pleurisy, endocarditis or septicemia, caused by *Streptococcus pneumonia*.

In other embodiments of the present invention, the infection is puerperal septicopyemia in pregnant women, neonatal meningitis, postpartum infection, bacteremia, endocarditis, skin and soft tissue infection or osteomyelitis, caused by *Streptococcus agalactiae*.

In other embodiments of the present invention, the infection is a cardiovascular system infection or urinary tract infection, caused by *Enterococcus*.

In other embodiments of the present invention, the infection is a urinary tract infection, pyogenic abdominal infection, septicemia, endocarditis or diarrhea fever, caused by *Enterococcus faecium*.

In other embodiments of the present invention, the infection is endocarditis, cholecystitis, meningitis, urinary tract infection or wound infection, caused by *Enterococcus faecalis*.

In other embodiments of the present invention, the infection is epidemic encephalomyelitis caused by *Neisseria meningitides*.

In other embodiments of the present invention, the infection is gonorrhea caused by *Neisseria gonorrhoeae*.

In other embodiments of the present invention, the infection is a urinary system infection, parenteral pyogenic infection, intestinal infection or hemorrhagic colitis, caused by *Escherichia*.

In other embodiments of the present invention, the infection is bacillary dysentery caused by *Shigella*.

In other embodiments of the present invention, the infection is typhia and paratyphoid caused by *Salmonella*.

In other embodiments of the present invention, the infection is pneumonia, bronchitis, urinary tract infection, wound infection, meningitis or peritonitis, caused by *Klebsiella pneumoniae*.

In other embodiments of the present invention, the infection is antibiotic-associated hemorrhagic colitis caused by *Klebsiella oxytoca*.

In other embodiments of the present invention, the infection is pneumonia or meningitis caused by *Citrobacter*.

In other embodiments of the present invention, the infection is skin soft tissue infection, urinary tract infection, respiratory tract infection, abdominal infection, central nervous system infection, eye infection, wound infection, endocarditis or septicemia, caused by *Enterobacter cloacae*.

In other embodiments of the present invention, the infection is pneumonia, urinary tract infection, bacteremia or postoperative infection, caused by *Serratia*.

In other embodiments of the present invention, the infection is tetanus caused by *Clostridium tetani*.

In other embodiments of the present invention, the infection is a clinical infection such as gas gangrene or food poisoning caused by *Clostridium perfringens*.

In other embodiments of the present invention, the infection is an abdominal infection, female reproductive tract and pelvic infection or bacteremia, caused by asporous anaerobic bacterium.

In other embodiments of the present invention, the infection is diphtheria caused by *Corynebacterium diphtheria*.

In other embodiments of the present invention, the infection is acne, comedo caused by *Corynebacterium acnes*.

In other embodiments of the present invention, the infection is a wound infection, burn tissue infection and other local pyogenic infections, lung infection, urinary tract infection, otitis media, keratitis, endocarditis or septicemia, caused by *Pseudomonas aeruginosa*.

In other embodiments of the present invention, the infection is a respiratory tract infection, bacteremia, urinary tract infection, secondary meningitis, surgical site infection or ventilator-associated pneumonia, caused by *Acinetobacter baumannii*.

In other embodiments of the present invention, the infection is pertussis caused by *Bordetella pertussis*.

In other embodiments of the present invention, the infection is bacteremia in infants and children, acute bacterial meningitis, cellulitis, osteomyelitis or joint infection, caused by *Haemophilus* like *Haemophilus* influenza.

In other embodiments of the present invention, the infection is tuberculosis caused by *Mycobacterium tuberculosis*.

In other embodiments of the present invention, the infection is a chronic refractory infection wound surface.

In other embodiments of the present invention, the use of the polypeptides for the manufacture of a medicament for the prevention and/or treatment of eczema is provided.

The present invention further provides the use of a polypeptide for the manufacture of a medicament for the promotion of tissue repair and/or wound healing, wherein the polypeptide has any one of the amino acid sequences as set forth in (I) and (II):

(I) the amino acid sequence as set forth in SEQ ID NO: 1; and (II) amino acid sequences obtained from the amino acid sequence as set forth in SEQ ID NO: 1 with modification, substitution, deletion or addition of one or more amino acids;

wherein the modification includes amidation, phosphorylation, methylation, acetylation, ubiquitination, glycosylation or carbonylation; the substitution is substitution of 1, 2, 3, 4 or 5 amino acids; the deletion is deletion of 1, 2, 3, 4 or 5 amino acids; the addition is addition of 1, 2, 3, 4, 5, 6, 7, 8, 9 or 10 amino acids, and the polypeptide does not have the amino acid sequence as set forth in SEQ ID NO: 4, SEQ ID NO: 5, SEQ ID NO: 6, SEQ ID NO: 53 or SEQ ID NO: 54. Preferably, the polypeptide has the amino acid sequence as set forth in SEQ ID NO: 2.

The present invention further provides the use of the polypeptide for the manufacture of a medicament for the treatment of burn injury, cold injury, crush injury, war injury, animal bite, nuclear radiation injury or combined injury, wherein the polypeptide has any one of the amino acid sequences as set forth in (I) and (II):

(I) the amino acid sequence as set forth in SEQ ID NO: 1;

(II) amino acid sequences obtained from the amino acid sequence as set forth in SEQ ID NO: 1 with modification, substitution, deletion or addition of one or more amino acids;

wherein the modification includes amidation, phosphorylation, methylation, acetylation, ubiquitination, glycosylation or carbonylation; the substitution is substitution of 1, 2, 3, 4 or 5 amino acids; the deletion is deletion of 1, 2, 3, 4 or 5 amino acids; the addition is addition of 1, 2, 3, 4, 5, 6, 7, 8, 9 or 10 amino acids; and the polypeptide does not have the amino acid sequence as set forth in SEQ ID NO: 4, SEQ ID NO: 5, SEQ ID NO: 6, SEQ ID NO: 53 or SEQ ID NO: 54. Preferably, the polypeptide has the amino acid sequence as set forth in SEQ ID NO: 2.

The present invention further provides a DNA molecule encoding the polypeptide as described above, which has any one of nucleotide sequences as set forth in I and II:

I. the nucleotide sequence as set forth in SEQ ID NO: 3;

II. nucleotide sequences obtained from the nucleotide sequence as set forth in SEQ ID NO: 3 with modification, substitution, deletion or addition of one or more bases.

The present invention provides the construction of a cDNA library of the venom gland tissue from *Chaerilus tryznai* Kovarik with high quality, specifically comprising the steps of: separating total RNA and purifying mRNA from the venom gland of *Chaerilus tryznai* Kovarik, synthesizing the first and second chains of cDNA, ligating and transforming into the double-strand cDNA and pSPORT1 vector, and obtaining the cDNA library of the venom gland tissue from *Chaerilus tryznai* Kovarik. Based on the library as constructed, 3000 clones were randomly selected and sequenced, among which the 2007$^{th}$ clone was found to be a novel gene encoding the antiseptic peptide from *Chaerilus tryznai* Kovarik by sequence analysis, named Ctryamp and having the nucleotide sequence as set forth in SEQ ID NO: 3:

```
ttcctctgtgaaagtaagttctgtgaaactcactcttcgataaaatgaa atctcagacctattccttcttttctagttgttttattattagcaattt cacaatcagaagcttttatcaggatcgccaggctcctcaggatctttgg aaaaagaagtatgagagatatggatactatgaaatacttatatgaacca agtagagtgcagctgacttgaaaaccttacaaaaactaatggaaaatta ctgattatttgaatataataatgttatctctattttagattataaatat ttcttttgaaaaaaaaaaaaaaaaaaaaa
```

(FIG. 1).

The present invention further provides a recombinant vector comprising the DNA molecule as described above.

The present invention further provides a method for preparing the polypeptide, comprising the steps of:

obtaining a DNA molecule encoding the amino acid sequence as set forth in (I) or (II), wherein (I): the amino acid sequence as set forth in SEQ ID NO: 1, and (II): amino acid sequences obtained from the amino acid sequence as set forth in SEQ ID NO: 1 with modification, substitution, deletion or addition of one or more amino acids;

fusing the DNA molecule with an expression vector to construct a recombinant expression vector;

transforming the recombinant expression vector into a host cell to obtain a transformant; and inducing the transformant to express a protein, and then performing the separation and purification to obtain the product.

In some embodiments of the present invention, the DNA molecule in the method for preparing the polypeptide is any one of the nucleotide sequences as set forth in I and II:

I. the nucleotide sequence as set forth in SEQ ID NO: 3;

II. nucleotide sequences obtained from the nucleotide sequence as set forth in SEQ ID NO: 3 with modification, substitution, deletion or addition of one or more bases.

In some embodiments of the present invention, the host cell is a prokaryotic host cell or eukaryotic host cell.

Preferably, the prokaryotic host cell is *Escherichia coli*.

The present invention further provides a pharmaceutical formulation for the treatment of a wound surface infection and/or the promotion of tissue repair and healing consisting of a polypeptide and a pharmaceutically acceptable carrier, in which the polypeptide has any one of the amino acid sequences as set forth in (I) and (II):

(I) the amino acid sequence as set forth in SEQ ID NO: 1;

(II) amino acid sequences obtained from the amino acid sequence as set forth in SEQ ID NO: 1 with modification, substitution, deletion or addition of one or more amino acids;

wherein the modification includes amidation, phosphorylation, methylation, acetylation, ubiquitination, glycosylation or carbonylation; the substitution is substitution of 1, 2, 3, 4 or 5 amino acids; the deletion is deletion of 1, 2, 3, 4 or 5 amino acids; the addition is addition of 1, 2, 3, 4, 5, 6, 7, 8, 9 or 10 amino acids; and the polypeptide does not have the amino acid sequence as set forth in SEQ ID NO: 4, SEQ ID NO: 5, SEQ ID NO: 6, SEQ ID NO: 53 or SEQ ID NO: 54. Preferably, the polypeptide has the amino acid sequence as set forth in SEQ ID NO: 2. In some embodiments of the present invention, the polypeptide accounts for 0.01%~1.5% by weight of the pharmaceutical formulation.

In some embodiments of the present invention, the carrier includes hydroxypropylmethylcellulose, which accounts for 7.0% by weight of the pharmaceutical formulation.

Preferably, by weight, the pharmaceutical formulation provided in the present invention consists of 0.01%~1.5% polypeptide, 5% glycerol, 7% hydroxypropylmethyl cellulose, 0.1% glycolic acid, 0.1% EDTA, with the balance of water.

Preferably, the pharmaceutical formulation provided in the present invention is a gel, powder for injection, aerosol, spray, liniment, film, patch, cream, ointment, adhesive plaster, liquid, decoction, granule, tablet, pill, sustained-release agent, controlled-release agent, powder, paste, liniment, lotion, smeared film, penetration ions, eye drop, nasal drop, gargle, sublingual tablet, insufflating agent, suppository, aerosol, inhalant, fumicant, oral solution, oral tablet, injection, syrup, electuary, vinum, pulvis, granule, pill, tablet, capsule, enema or suppository.

The present invention further provides the use of a polypeptide for the manufacture of a feed, health product, food and cosmetic additive, wherein the polypeptide has any one of the amino acid sequences as set forth in (I) and (II):

(I) the amino acid sequence as set forth in SEQ ID NO: 1;

(II) amino acid sequences obtained from the amino acid sequence as set forth in SEQ ID NO: 1 with modification, substitution, deletion or addition of one or more amino acids;

wherein the modification includes amidation, phosphorylation, methylation, acetylation, ubiquitination, glycosylation or carbonylation; the substitution is substitution of 1, 2, 3, 4 or 5 amino acids; the deletion is deletion of 1, 2, 3, 4 or 5 amino acids; the addition is addition of 1, 2, 3, 4, 5, 6, 7, 8, 9 or 10 amino acids; and the polypeptide does not have the amino acid sequence as set forth in SEQ ID NO: 4, SEQ ID NO: 5, SEQ ID NO: 6, SEQ ID NO: 53 or SEQ ID NO: 54. Preferably, the polypeptide has the amino acid sequence as set forth in SEQ ID NO: 2.

The present invention provides a polypeptide having any one of the amino acid sequences as set forth in (I) and (II):

(I) the amino acid sequence as set forth in SEQ ID NO: 1;

(II) amino acid sequences obtained from the amino acid sequence as set forth in SEQ ID NO: 1 with modification, substitution, deletion or addition of one or more amino acids. The antiseptic results show that, the synthetic Ctryamp polypeptide and the structurally homologous polypeptides thereof have potent inhibitory effect on the growth of a standard gram-negative bacterium *Escherichia coli* CCTCCAB94012 and gram-positive bacterium *Staphylococcus aureus* CCTCCAB94014. At 6.25 µg/mL, the Ctryamp polypeptide and structurally homologous polypeptides thereof have an inhibition rate of 100% on the *Escherichia coli* CCTCCAB94012; while at 6.25 µg/mL, have an inhibition rate of 100% on the *Staphylococcus aureus* CCTCCAB94014 (Table 3). Further antiseptic results show that, the synthetic Ctryamp polypeptide has potent inhibitory effect on the proliferation of a gram-negative bacterium, in particular pathogenic *Escherichia coli* and *Pseudomonas aeruginosa* (Table 3), in which the Ctryamp polypeptide has a minimal inhibitory concentration of 8-16 µg/mL on *Pseudomonas aeruginosa*. The antiseptic results also show that, the chemically synthesized Ctryamp polypeptide has potent inhibitory effect on the proliferation of a gram-positive bacterium (Table 3). The antiseptic results show that, the Ctryamp polypeptide has potent inhibitory effect on the growth of anaerobic bacterium (Table 3). The Ctryamp polypeptide has potent inhibitory effect on clinically drug-resistant bacteria (methicillin-resistant *Staphylococcus aureus*, methicillin-resistant coagulase-negative staphylococci, erythromycin-resistant *Streptococcus pyogenes*, ESBL-producing *Escherichia coli* resistant to penicillin and cephalosporins, to monoamides, having cross drug-resistance to quinolones, aminoglycosides, sulfonamides, imipenem-resistant *Pseudomonas aeruginosa* (IPM-R strain)) (Table 3). The Ctryamp polypeptide has potent inhibitory effect on bacteria causing specific infections (including *Bordetella pertussis, Clostridium tetani, Clostridium perfringens, Shigella, Salmonella typhi* and *Corynebacterium diphtheria*) (Table 3).

The present invention further provides a topical antiseptic gel formulation. The antiseptic results showed that, the antiseptic formulation had potent inhibitory effect on gram-positive bacteria, gram-negative bacteria, anaerobic bacterium and clinically drug-resistant bacteria. The antiseptic formulation has a minimal inhibitory concentration MIC of 6.25 µg/mL against the standard gram-negative bacterium *Escherichia coli* CCTCCAB94012, has a minimal inhibitory concentration MIC of 6.25 µg/mL against the gram-positive bacterium *Staphylococcus aureus* CCTCCAB94004, has a minimal inhibitory concentration MIC of 6.25 µg/mL against methicillin-resistant *Staphylococcus aureus*, has a minimal inhibitory concentration MIC of 8 µg/mL against *Pseudomonas aeruginosa*, and has a minimal inhibitory concentration MIC of 25 µg/mL against *Clostridium perfringens* (Table 4) (calculated based on the active ingredient antiseptic Ctryamp polypeptide or the structurally homologous polypeptides thereof for the formulation).

Patients with various traumas and patients with chronic refractory infection wound surfaces on the body surface coming to hospital for treatment were selected. They were randomly divided into an experimental group and a control group. The experimental group was administered with the topical Ctryamp polypeptide antiseptic gel formulation as prepared, while the control group was administered with conventional drug (administered with 5% Sulfur Cream). For bacterial infections on the wound surface, all of the 82 patients in the treatment group experienced wound surface healing in the first phase, without any infections or delayed healing of the wound surface, and without any allergic reaction or other adverse reactions. In accordance with the Antibacterial Drug Clinical Trial Technical Standards issued by the Ministry of Health in 1988, four ranks are divided to evaluate efficacy: healing, significant, effective, ineffective. Results showed that in the 82 cases of the treatment group, 80 cases were significant and 2 cases were effective, giving an effective rate of 100%. In the 74 cases of the control group, 50 cases were significant, 20 cases effective and 4 cases ineffective, giving an effective rate of 95%. Statistical F-test between two groups was significant, $p<0.05$. Comparison of time for the promotion of wound surface healing between the two groups is shown in Table 5. By statistical F-test, $p<0.05$. Clinical treatment results showed that the topical gel provided in the present invention is capable of effectively preventing and treating bacterial infections, with unique antiseptic effect on MRSA and imipenem-resistant *Pseudomonas aeruginosa* (IPM-R strain) in particular, while is capable of significantly promoting repair and healing of a wound.

For clinical observation of acne treatment, 258 patients with acne, pimple, comedo were selected as the subjects. The number of facial acne skin damages, the changes and adverse reactions were recorded with the patients of the two groups, an experimental group (treated with a topical Ctryamp polypeptide antiseptic gel formulation) and a control group. The efficacy was analysized based on the total percentage of reduction of various damages (comedo, inflammatory scars, abscesses, nodules or cystides) caused by acne. In the experimental group with an antiseptic formulation against *Propionibacterium acnes*, the effective rate was 97%, while it was 41% in the control group with conventional administration. There was highly significant difference in effective rate between the two groups, suggesting that the efficacy on acne treatment in the experimental group was superior to the control group.

In the Burn and Plastic Surgery Unit of the People's Hospital of Hubei Province, 22 patients with chronic eczema were treated with the topical Ctryamp polypeptide antiseptic gel formulation of the present invention. The experimental results showed that, the antiseptic gel of the peptide from Chaerdus tryznai Kovarik had a unique efficacy in treating eczema, with a curative rate of 100%. During the clinical follow-up visits, there was no relapse; whereas in the experimental group, clinical symptoms were reduced but there were severe relapses during follow-up visits.

The present invention further provides a novel medicament, which is more effective in treating wound surface bacterial infection, acne and eczema. The novel medicament is formulated with an active polypeptide from the traditional Chinese medicinal material scorpion as an active ingredient. The medicament has significant therapeutic effect for the treatment of wound surface bacterial infections, chronic refractory infection wound surfaces on the body surface, acne and eczema, and for the promotion of tissue repair and wound healing. The present invention also relates to an additive for the prevention of bacterial infections and promotion of tissue repair, which is useful for the manufacture of a cosmetic, health product and feed, with significant effect on the prevention of bacterial infections and the promotion of skin tissue repair. The raw materials employed in the present invention are all active ingredients in the traditional Chinese medicinal material scorpion, with no toxic side effect and no sequel. Such a medicament or additive is capable of truly taking effect rapidly, with no side effects and no relapses after treatment.

BRIEF DESCRIPTION OF THE DRAWINGS

FIG. 1 shows the gene sequence (SEQ ID NO: 3) of the broad-spectrum antiseptic active Ctryamp polypeptide from *Chaerilus tryznai* Kovarik provided in the present invention.

FIG. 2 shows the purity of the antiseptic active Ctryamp polypeptide from *Chaerilus tryznai* Kovarik.

DETAILED DESCRIPTION OF THE INVENTION

Figure 3:
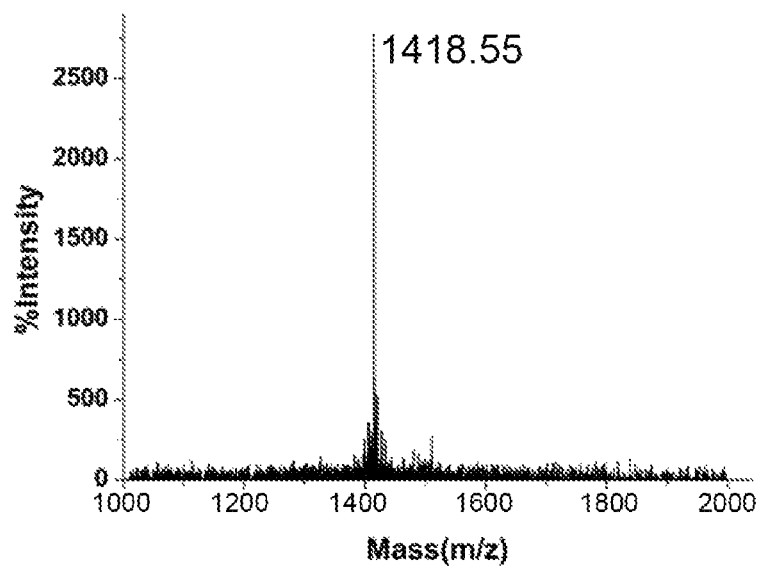
FIG. 3 shows a mass spectrum of the antiseptic active Ctryamp polypeptide from *Chaerilus tryznai* Kovarik.

The present invention discloses a polypeptide, DNA molecule encoding the polypeptide, vector, preparation method and use, which can be embodied by those skilled in the art through suitable modifications of the process parameters in view of the disclosure herein. It is to be particularly indicated that, all similar substitutions and alterations are obvious to those skilled in the art, which will be deemed to be included in the present invention. The method and use of the present invention has been described by ways of preferred examples. Thus, those skilled in the art can embody and apply the technology of the present invention by alteration, suitable change or combination of the method and use as described in the present invention, without departing from the content, spirit and scope of the present invention.

The present invention will be further illustrated in conjunction with examples in the following.

Example 1: Preparation of the Gene for the Broad-Spectrum Antiseptic Active Polypeptide from *Chaerilus Tryznai* Kovarik A: Extraction of total RNA from the venom gland of *Chaerilus tryznai* Kovarik (Trizol LS one-step method: Trizol LS was purchased from Invitrogen, USA)

(1) 500 mg of the venom gland from the scorpion's tail was ground into fine powders in liquid nitrogen, added with 10 mL of TRIZOL reagent with well mixing, and placed at room temperature (20-25° C., the same as hereinafter) for 5 min. (2) 2 mL chloroform was then added with mixing for 15 s, placed at room temperature for 2-3 min, and centrifuged at 12000 g and 4° C. for 15 min. (3) The aqueous phase was taken out and added with same volume of isopropanol, then placed at room temperature for 10 min, and centrifuged at 12000 g and 4° C. for 10 min to obtain RNA precipitate. (4) The precipitate was washed with 5 ml of 75% ethanol and centrifuged at 7500 g for 5 min. (5) The RNA precipitate was dried followed by dissolution in DEPC treating water, kept at 55-60° C. for 10 min to completely dissolve RNA. All the process was performed in accordance with the method recommended by TRIZOL (Total RNA Isolation) Reagent Kit. The quality of the prepared total RNA from the scorpion venom gland was detected by using formaldehyde-denatured gel electrophoresis. High-quality total RNA from the scorpion venom gland was obtained.

B: Separation and purification of mRNA mRNA was separated and purified by using a PolyA Trace mRNA separation system (Promega, USA), the operating principle of which was that, based on the property of complementary pairing between the Oligo(dT) and poly(A) tail at 3' end of the mRNA, Oligo(dT) was labeled with biotin and formed a hybrid with the poly(A) at 3' end of the mRNA through annealing, and then the biotin Oligo(dT)/ mRNA hybrid was captured and washed by magnetic beads labeled with avidin and a magnetic separation rack, and finally eluted with sterilized double distilled water (ddH$_2$O) free of a RNA enzyme, thus to separate mRNA from the total RNA. (1) Sample preparation: The RNA was added into 800 μL binding buffer containing 32 μL β-mercaptoethanol. (2) Probe annealing: 5 μL of Oligo(dT) at a concentration of 250 μM was added with distilled water up to 50 μL; and added with 1.6 mL preheated dilution buffer (a dilution buffer added with 32 μL β-mercaptoethanol), mixed with RNA uniformly and incubated at 70° C. for 5 min. (3) Magnetic bead activation: 1.2 mL magnetic beads SA-PMPS (purchased from Promega, USA) was charged into a 1.5 mL centrifuge tube and resuspended with 0.5×SSC, the magnetic beads was absorbed on the magnetic rack and SA-PMPS was washed with 0.5×SSC in the original volume three times. (4) mRNA acquisition: RNA incubated at 70° C. was mixed with SA-PMPS, placed at room temperature for 5 min, and then on the magnetic rack for magnetic bead absorption, with the supernatant removed; the magnetic bead with 2 mL of 0.5×SSC, washed repeatedly twice, with SSC being removed to the greatest extent in the last time, and then added with ddH$_2$O free of a RNA enzyme with mixing gently and uniformly, centrifuged (12000 g×3 min) or absorbed on the magnetic rack; the supernatant was taken to obtain mRNA. The mRNA was determined by electrophoresis and ultraviolet for its concentration and purity. (5) mRNA precipitation: the mRNA obtained in (4) was added with anhydrous ethanol with a volume of 2.5 times and glycogen for precipitation overnight. The mRNA was used for cDNA synthesis.

C: Synthesis of the first strand of cDNA (1) Into a 1.5 mL Ep tube 2 μL Not I Primer-adapter and 6 μL mRNA (comprising 3 mRNA) were added, incubated at 70° C. for 10 min and rapidly placed onto ice; after centrifugation, the following ingredients were added: 4 μL 5× first strand buffer; 2 μL 0.1 M DTT; 1 μL 10 mM dNTPs, 1 μL H$_2$O, followed by mixing gently and centrifugation, it was left at 37° C. for 2 min. (2) 5 μL reverse transcriptase was added, and mixed uniformly; 2 μL of the solution was added with 1 μL [α-$^{32}$P]dCTP (4 μCi) (tracing tube). Simultaneously with the above reaction components (sample tube), the tracing tube was incubated at 37° C. for 1 hour and then placed onto ice for stopping the reaction. (3) For the tracing tube, 43 μL 20 mM EDTA and 5 μL yeast tRNA was added in sequence, and after mixed uniformly, two 10 μL samples were taken out respectively and pointed on two filter membranes, in which one was washed with 10% TCA three times, each for 5 min, with 95% ethanol once, dried in the air and placed into 1.5 mL scintillation solution (Sample 1); while the other was dried in the air and placed into 1.5 mL scintillation solution (Sample 2). Additional 30 μL tracing solution was added with 1.5 μL 7.5 M ammonium acetate (NH$_4$Oac) and 90 μL anhydrous ethanol (-20° C.), and centrifuged at 14,000 rpm for 20 min immediately after bing mixed uniformly, with the supernatant discharged; the precipitate was added with 0.5 mL 70% anhydrous ethanol (-20° C.), centrifuged at 14,000 rpm for 2 min, with the supernatant discharged, and then dried at 37° C. for 10 min to allow volatilization of ethanol, dissolved in 10 μL TEN solution and added with 10 μL 2× loading buffer, with 10 μL taken for basic gel electrophoresis. λDNA HindIII fragments were labeled with [α-$^{32}$P]dCTP for use as molecular weight markers. (4) After being mixed uniformly, it was placed at room temperature for 15 min, added with 2 μL 0.2 M EDTA to stop the reaction. 6 μL of the reaction solution was mixed with 6 mL 2× basic gel electrophoresis buffer uniformly, and after electrophoresis for 5 h, soaked in 7% TCA for 20 min until bromphenol blue became yellow, which was suck dry by hygienic papers (for about 8 h) to go through autoradiography. (5) For the sample tube, it was used for synthesis of a second chain.

| | |
|---|---|
| Hind III 10X buffer | 2 μL |
| dGTP | 0.2 mM |
| dATP | 0.2 mM |
| [α-$^{32}$P]dCTP | 2 μCi |
| Hind III markers | 1 μg |
| Klenow DNA polymerase | 2 unit |
| Total volume with ddH$_2$O addition | 20 μL |

D. Synthesis of the second strand of cDNA (1) On the ice the following ingredients were added into the sample tube. (2) After being mixed gently until a uniform, it was incubated at 16° C. for 2 h. (3) 2 μL (10 units) T$_4$DNA polymerase was added to continue the reaction at 16° C. for 5 min. (4) It was transferred onto the ice and added with 10 μL 0.5 M EDTA. (5) An equal volume (150 μL) phenol/chloroform/isoamylol (25/24/1) was added with complete vortex mixing and then centrifuged at 14,000 rpm and room temperature for 5 min. An aqueous phase (140 μL) was transferred into another 1.5 mL Ep tube. (6) 70 μL 7.5 M NH$_4$OAc and 0.5 mL anhydrous ethanol (-20° C.) were added, and after vortex mixing, centrifugation was performed at 14,000 rpm for 20 min at room temperature. (7) After the supernatant was discharged, 0.5 mL 70% ethanol (-20° C.) was added, followed by centrifugation for 2 min the same as above. With the supernatant discharged, the precipitate was dried at 37° C. for 10 min.

| | |
|---|---|
| DEPC-treated water | 92 μL |
| 5X second strand buffer | 30 μL |
| 10 mM dNTP mix | 3 μL |
| E. coli DNA ligase (10 units/μL) | 1 μL |
| E. coli DNA polymerase (10 units/μL) | 4 μL |
| E. coli RNase H (2 units/μL) | 1 μL |
| Total volume | 150 μL |

E. Ligation of double-strand cDNA with Sal I adapters (1) The cDNA sample in D was dissolved with 25 μL sterilized water, and then added with ingredients in the table below in sequence. (2) After being mixed gently into a uniform, reaction was carried out at 16° C. overnight (about 20 h). (3) After being extracted with phenol/chloroform/isoamylol (25/24/1) and precipitated with NH$_4$Oac/ethanol, it was dried at 37° C. for 10 min.

| | |
|---|---|
| 5X T$_4$DNA ligase buffer | 10 μL |
| Sal I adapters | 10 μL |
| T$_4$DNA ligase | 5 μL |
| Total volume | 50 μL |

F: Digestion of double-strand cDNA with Not I (1) The sample in E was dissolved in 4 μL, and then added with ingredients in the table below in sequence. (2) After being mixed uniformly, it was incubated at 37° C. for 2 h. (3) It was extracted with phenol/chloroform/isoamylol (25/24/1) once and then precipitated with 7.5 M NH$_4$Oac/ethanol, dried at 37° C. for 10 min. (4) It was dissolved in 70 μL TEN, with 1 μL for quantitation, and the remaining being stored at -20° C. for further use.

| | |
|---|---|
| REACT 3 buffer | 5 μL |
| Not I | 4 μL |
| Total volume | 50 μL |

G: Removal of excess Sal I adaptors and enzymatically digested small fragments from the double-strand cDNA molecule Excess Sal I adaptors and enzymatically digested small fragments were removed by using a nucleon extraction and purification kit (Amersham, USA). (1) Resins were suspended at room temperature, in which 600 μL was added onto a centrifugal column for centrigugation at 2000 rpm for 10 s, with the liquid removed. 40 μL of the above cDNA solution was added in the center of the resins and centrifuged the same as above. (2) The eluted solution was collected for a ligation reaction.

H: Ligation and transformation of double-strand cDNA and a pSPORT1 vector (1) The following ingredients were added into a 1.5 mL Ep tube in sequence. (2) Reaction was carried out at room temperature for 16 h. (3) The following ingredients were added in the reaction solution of (2) in sequence: 5.0 μL yeast tRNA, 12.5 μL 7.5 M NH4Oac, 70 μL anhydrous ethanol (-20° C.). Immediately after vortex mixing uniformly, centrifugation was carried out at 14000 for 20 min. (4) The precipitate was washed with 70% ethanol (-20° C.), dried at 37° C. and dissolved to 4 μL. (5) 2 μL was electroporated into 50 μL E. coli K12 MC1061. The quality of the library was identified by a PCR method, with a forward primer: 5'TCGACCCACGCGTCCG 3' (SEQ ID NO: 70) (designed based on the sequence of the Sal I adaptor) and a reverse primer: 5' GAGCGGCCGCCCT15 3' (SEQ ID NO: 71) (designed based on the sequence of the NotI primer-adaptor).

| | |
|---|---|
| 5X T₄ DNA ligase buffer | 4 µL |
| pSPORT1, Not I-Sal I-Cut (50 ng/µL) | 1 µL |
| cDNA (3 ng/µL) | 4 µL |
| T₄DNA ligase | 1 µL |
| Total volume with ddH₂O addition | 20 µL |

I: cDNA library screening with a random sequencing strategy 3000 clones were selected randomly from the well-constructed cDNA library for the venom gland from *Chaerilus tryznai* Kovarik, and were sent to Shanghai Sciample Company for sequencing. The sequence input software was BioEdit v4.5.8 (Tom Hall, 1999), and the prediction softwares for homology comparison and signal peptide cleavage sites were CLUSTAL X 1.8 (Thompson et al., 1997) and PC/GENE (Intelligenetics Inc., Switzerland), respectively. Sequence analysis indicated that, the 2007' clone was a novel antiseptic peptide gene, named Ctryamp, of which the sequence is the nucleotide sequence as set forth in SEQ ID NO: 3:

ttcctctgtgaaagtaagttctgtgaaactcactcttcgataaaatgaa atctcagaccttttccttcttttctagttgttttattattagcaatt tcacaatcagaagcttttatcaggatcgccaggctcctcaggatctttg gaaaaagaagtatgagagatatggatactatgaaatacttatatgaacc aagtttgagtgcagctgacttgaaaaccttacaaaaactaatggaaaat tactgattatttgaatataataatgttatctctattttagattataaat atttcttttgaaaaaaaaaaaaaaaaaaaaa (FIG. 1).

A precursor organizational form of the Ctryamp encodes 68 amino acid residues consisting of three portions, that is, a signal peptide (23 residues), mature peptide (11 residues) and precursor peptide (34 residues). Therefore, the present invention provides an antiseptic peptide from *Chaerilus tryznai* Kovarik: FIRIARLLRIF (SEQ ID NO: 2).

Example 2: Structure Analysis of Ctryamp Polypeptide and the Structurally Homologous Amphiphilic Polypeptides Thereof According to the sequence (FIRIARLLRIF (SEQ ID NO: 2)) of the mature peptide of Ctryamp as set forth in SEQ ID NO: 2 as provided in EXAMPLE 1, the secondary structure of Ctryamp was predicted by using on-line NPS@ server [DSC method (Discrimination of protein Secondary structure Class)], and shown by software AHTHEPROT 2000. Results showed that, the Ctryamp contained 100% of α-Helix structure, had a typical amphiphilic α-Helix structure and comprised a large number of basic residues (Arg) with net positive charges. Based on the helix diagram of the polypeptide sequence, a large number of point mutations on the polypeptide sequence FIRIARLLRIF (SEQ ID NO: 2) of Ctryamp were performed then. It was found that the sequence $FIX_1IAX_2LLX_3IF$ ($X_1$, $X_2$ and $X_3$ independently are any one of three basic amino acids His, Arg and Lys) (SEQ ID NO: 1) did not influence its amphiphilic property (Table 1). Therefore, the present invention provides a group of structurally homologous polypeptides (SEQ ID NO: 1) of a Ctryamp polypeptide from *Chaerilus tryznai* Kovarik.

TABLE 1

Ctryamp polypeptide from *Chaerilus tryznai* Kovarik and structurally homologous polypeptides thereof

| Polypeptide name | Amino acid sequence | Position in the Sequence listing | A Mutation property | helix value |
|---|---|---|---|---|
| Ctryamp | FIRIARLLRIF | SEQ ID NO: 2 | Wild type | 100% |
| Ctryamp-R3K | FIKIARLLRIF | SEQ ID NO: 7 | Basic | 100% |
| Ctryamp-R5K | FIRIAKLLRIF | SEQ ID NO: 8 | Basic | 100% |
| Ctryamp-R9K | FIRIARLLKIF | SEQ ID NO: 9 | Basic | 100% |
| Ctryamp-R3H | FIHIARLLRIF | SEQ ID NO: 10 | Basic | 100% |
| Ctryamp-R5H | FIRIAHLLRIF | SEQ ID NO: 11 | Basic | 100% |
| Ctryamp-R9H | FIRIARLLHIF | SEQ ID NO: 12 | Basic | 100% |
| Ctryamp-1 | FIKIAKLLRIF | SEQ ID NO: 13 | Basic | 100% |
| Ctryamp-2 | FIKIARLLKIF | SEQ ID NO: 14 | Basic | 100% |
| Ctryamp-3 | FIRIAKLLKIF | SEQ ID NO: 15 | Basic | 100% |
| Ctryamp-4 | FIKIAKLLKIF | SEQ ID NO: 16 | Basic | 100% |
| Ctryamp-5 | FIHIAHLLRIF | SEQ ID NO: 17 | Basic | 100% |
| Ctryamp-6 | FIHIARLLHIF | SEQ ID NO: 18 | Basic | 100% |
| Ctryamp-7 | FIHIAKLLRIF | SEQ ID NO: 19 | Basic | 100% |
| Ctryamp-8 | FIRIAKLLHIF | SEQ ID NO: 20 | Basic | 100% |

Example 3: Polypeptide and the Structurally Homologous Amphiphilic Polypeptides Thereof Artificial synthesis was carried out according to the amino acid sequence of the Ctryamp (FIRIARLLRIF (SEQ ID NO: 2)) as provided in EXAMPLE 1 and that of the structurally homologous amphiphilic polypeptides thereof ($FIX_1IAX_2LLX_3IF$ (SEQ ID NO: 1), as provided in EXAMPLE 2). A high-purity Ctryamp polypeptide (as shown in FIGS. 2 and 3) and structurally homologous amphiphilic polypeptides thereof were obtained by solid-phase chemical synthesis (Table 1).

Example 4: Bacteriostasis Experiment of Ctryamp Polypeptide and the Structurally Homologous Amphiphilic Polypeptides Thereof Bacteriostasis Experiment on Gram-Negative Bacteria:
96-well plate culturing method: (1) When *Pseudomonas aeruginosa* (including a standard strain, clinically isolated strain and drug resistant strain), *Escherichia coli* (including standard strains CCTCC AB94012 and ATCC25922, a clinically isolated strain and drug resistant strain), *Klebsiella pneumoniae, Serratia fonticola, Salmonella typhimurium, Shigella dysentery, Acinetobacter baumannii, Neisseria meningitidis, Neisseria gonorrhoeae, Bordetella pertussis* and *Haemophilus* influenza were cultured to OD600=0.8, respectively, they were diluted in 400 times and 80 μl of each was added into a 96-well plate, and then added with 20 μl of the Ctryamp polypeptide and structurally homologous amphiphilic polypeptides thereof (as provided in EXAMPLE 2) which were diluted with equal ratios, respectively, reaching final concentrations of 100 μg/ml, 10 μg/ml, 1 μg/ml, 0.1 μg/ml. 20 μl of liquid medium and 20 μl of kanamycin were respectively added into a negative control and positive control well (with a final concentration of 20 μg/ml). (2) After culture at 37° C. for 12 hours, each well in the 96-well plate was detected for absorbance at 600 nm with a microplate reader. (3) After the minimum inhibitory concentration of the 10-fold diluted drug, that is, the Ctryamp polypeptide and structurally homologous amphiphilic polypeptides thereof were determined, the minimum inhibitory concentration was double diluted and the steps (1) and (2) were repeated, thereby finally determining the minimum inhibitory concentration against bacteria of the antiseptic Ctryamp polypeptide and structurally homologous amphiphilic polypeptides thereof.

For the Ctryamp polypeptide as provided in EXAMPLE 1, MIC against *Pseudomonas aeruginosa* was 8 μg/ml, MIC against *Escherichia coli* was 6.25-12.5 μg/ml, MIC against *Klebsiella pneumoniae* was 25 μg/ml, MIC against *Serratia fonticola* was 12.5 μg/ml, MIC against *Salmonella typhimurium* was 12.5 μg/ml, MIC against *Shigella* dysentery was 6.25 μg/ml, MIC against *Acinetobacter baumannii* was 6.25 μg/ml, MIC against *Neisseria meningitidis* was 6.25 μg/ml, MIC against *Neisseria gonorrhoeae* was 6.25 μg/ml, MIC against *Bordetella pertussis* was 3.13 μg/ml, and MIC against *Haemophilus* influenza was 3.13 μg/ml. MIC against *Proteusbacillus vulgaris* was 6.25 μg/ml.

Bacteriostasis Experimenton Gram-Positive Bacteria:

96-well plate culturing method: (1) When *Staphylococcus aureus* (including standard strains CCTCC AB94004 and ATCC25923, a clinically isolated strain), methicillin-sensitive coagulase-negative staphylococci (MSSCNS), *Streptococcus* hemolyticus (including a standard strain, clinically isolated strain and drug resistant strain), *Enterococcus, Corynebacterium* diphtherias, *Corynebacterium acnes* were cultured to OD600=0.8, respectively, they were diluted in 400 times and 80 μl of each was added into a 96-well plate, and then added with 20 μl of the Ctryamp polypeptide and structurally homologous amphiphilic polypeptides thereof (as provided in EXAMPLE 2), which were diluted with equal ratios, respectively, reaching final concentrations of 100 μg/ml, 10 μg/ml, 1 μg/ml, 0.1 μg/ml. 20 μl of liquid medium and 20 μl of penicillin were respectively added into a negative control and positive control well (with a final concentration of 50 μg/ml). (2) After culture at 37° C. for 12 hours, each well in the 96-well plate was detected for absorbance at 600 nm with a microplate reader. (3) After the minimum inhibitory concentration of the 10-fold diluted drug, that is, the Ctryamp polypeptide and structurally homologous amphiphilic polypeptides thereof were determined, the minimum inhibitory concentration was double diluted and the steps (1) and (2) were repeated, to finally determine the minimum inhibitory concentration against bacteria of the antiseptic Ctryamp polypeptide and structurally homologous amphiphilic polypeptides thereof.

For the Ctryamp polypeptide and structurally homologous amphiphilic polypeptides thereof, MIC against *Staphylococcus aureus* was 1.63-6.25 μg/ml, against methicillin-sensitive coagulase-negative staphylococci of the Ctryamp polypeptide was 3.13-12.5 μg/ml, against *Streptococcus hemolyticus* was 8-16 μg/ml, against *Corynebacterium diphtheriae* was 3.13 μg/ml, against *Corynebacterium acnes* was 3.13 μg/ml, and against *Enterococcus* was 6.25 μg/ml.

Bacteriostasis Experiment on Methicillin-Resistant *Staphylococcus*:

Methicillin-resistant *Staphylococcus aureus* (MRSA) and methicillin-resistant coagulase-negative staphylococci (MRSCNS): clinical strains were separated and obtained from Clinical Laboratory Center in People's Hospital of Jiangsu, Central South University.

96-well plate culturing method: (1) When methicillin-resistant *Staphylococcus aureus* and methicillin-resistant coagulase-negative staphylococci were cultured to OD600=0.8, respectively, they were diluted in 400 times and 80 μl of each was added into a 96-well plate, and then added with 20 μl of the Ctryamp polypeptide and structurally homologous amphiphilic polypeptides thereof (as provided in EXAMPLE 2) which were diluted with equal ratios, respectively, reaching final concentrations of 100 μg/ml, 10 μg/ml, 1 μg/ml, 0.1 μg/ml. 20 μl of liquid medium and 20 μl of vancomycin were respectively added into a negative control and positive control well (with a final concentration of 12 μg/ml). (2) After culture at 37° C. for 12 hours, each well in the 96-well plate was detected for absorbance at 600 nm with a microplate reader. (3) After the minimum inhibitory concentration of the 10-fold diluted drug of the Ctryamp polypeptide was determined, the minimum inhibitory concentration was double diluted and the steps (1) and (2) were repeated. The minimum inhibitory concentration of the antiseptic Ctryamp polypeptide against methicillin-resistant *Staphylococcus aureus* and methicillin-resistant coagulase-negative staphylococci was 3.13-12.5 μg/ml or 4-8 μg/ml (Test results from the third party).

Bacteriostasis experiment on anaerobic bacterium:

96-Well Plate Culturing Method: (1) when *Clostridium tetani, Clostridium perfringens, Bacteroides fragilis* were cultured to OD600=0.8, respectively, they were diluted in 400 times and 80 μl of each was added into a 96-well plate, and then added with 20 μl of the Ctryamp polypeptide as provided in EXAMPLE 1 which was diluted with equal ratios, respectively, reaching final concentrations of 100 μg/ml, 10 μg/ml, 1 μg/ml, 0.1 μg/ml. 20 μl of liquid medium and 20 μl of penicillin were respectively added into a negative control and positive control well (with a final concentration of 400 μg/ml). (2) After culture at 37° C. for 12 hours, each well in the 96-well plate was detected for absorbance at 600 nm with a microplate reader. (3) After the minimum inhibitory concentration of the 10-fold diluted drug, that is, the Ctryamp polypeptide and structurally homologous amphiphilic polypeptides thereof was determined, the minimum inhibitory concentration was double diluted and the steps (1) and (2) were repeated, thereby finally determining the minimum inhibitory concentration against bacteria of the antiseptic Ctryamp polypeptide.

For the Ctryamp polypeptide, MIC against *Clostridium tetani* was 25 μg/ml, against *Clostridium perfringens* was 25 μg/ml, and against *Bacteroides fragilis* was 12.5 μg/ml.

Results of the antiseptic tests are shown in Tables 2, 3 and 4.

TABLE 2

Minimum inhibitory concentration MIC (μg/ml) of Ctryamp polypeptide from *Chaerilus tryznai* Kovarik and the structurally homologous polypeptides thereof against standard *Escherichia coli* and *Staphylococcus aureus*

| Polypeptide name | Amino acid sequence | *Escherichia coli* | *Staphylococcus aureus* |
| --- | --- | --- | --- |
| Ctryamp | FIRIARLLRIF (SEQ ID NO: 55) | 12.5 | 6.25 |
| Ctryamp-R3K | FIKIARLLRIF (SEQ ID NO: 56) | 12.25 | 6.25 |
| Ctryamp-R5K | FIRIAKLLRIF (SEQ ID NO: 57) | 6.25 | 6.25 |
| Ctryamp-R9K | FIRIARLLKIF (SEQ ID NO: 58) | 12.5 | 6.25 |
| Ctryamp-R3H | FIHIARLLRIF (SEQ ID NO: 59) | 6.25 | 6.25 |
| Ctryamp-R5H | FIRIAHLLRIF (SEQ ID NO: 60) | 12.5 | 6.25 |
| Ctryamp-R9H | FIRIARLLHIF (SEQ ID NO: 61) | 6.25 | 6.25 |
| Ctryamp-1 | FIKIAKLLRIF (SEQ ID NO: 62) | 6.25 | 6.25 |
| Ctryamp-2 | FIKIARLLKIF (SEQ ID NO: 63) | 6.25 | 12.5 |
| Ctryamp-3 | FIRIAKLLKIF (SEQ ID NO: 64) | 12.5 | 6.25 |
| Ctryamp-4 | FIKIAKLLKIF (SEQ ID NO: 65) | 6.25 | 12.5 |
| Ctryamp-5 | FIHIAHLLRIF (SEQ ID NO: 66) | 6.25 | 12.5 |
| Ctryamp-6 | FIHIARLLHIF (SEQ ID NO: 67) | 6.25 | 6.25 |
| Ctryamp-7 | FIHIAKLLRIF (SEQ ID NO: 68) | 12.5 | 6.25 |
| Ctryamp-8 | FIRIAKLLHIF (SEQ ID NO: 69) | 12.5 | 6.25 |

TABLE 3

The inhibitory effect of Ctryamp polypeptide from *Chaerilus tryznai* Kovarik on gram-negative and positive bacteria, anaerobic bacterium and clinically drug-resistant bacteria

| Bacterial (family) genus | Experimental bacteria | Nature | Number of experimental strains | Minimum inhibitory concentration MIC (μg/ml) |
| --- | --- | --- | --- | --- |
| *Staphylococcus* | *S. aureus* (standard strain ATCC25923) | G$^+$ | 1 | 6.25 |
| | *S. aureus* (clinically isolated strain) | G$^+$ | 17 | 1.63-6.25 |
| | Methicillin-resistant *S. aureus* (MRSA) | G$^+$ | 5 | 3.13-12.5 |
| | ★*S. aureus* ATCC 29213 | G$^+$ | 1 | 8 |
| | ★Methicillin-resistant *S. aureus* (MRSA) | G$^+$ | 11 | 4-8 |
| | ★methicillin-resistant coagulase-negative staphylococci (MRSCNS) | G$^+$ | 11 | 4 |
| | ★methicillin-sensitive coagulase-negative staphylococci (MSSCNS) | G$^+$ | 5 | 4 |
| *Streptococcus* | *S. pneumoniae* | G$^+$ | 1 | 3.13 |
| | *S. agalactiae* | G$^+$ | 1 | 25 |
| | ★*Streptococcus* ATCC 19615 (standard strain) | G$^+$ | 1 | 8 |
| | ★Erythromycin-sensitive *S. pyogenes* | G$^+$ | 4 | 16 |

TABLE 3-continued

The inhibitory effect of Ctryamp polypeptide from *Chaerilus tryznai* Kovarik on gram-negative and positive bacteria, anaerobic bacterium and clinically drug-resistant bacteria

| Bacterial (family) genus | Experimental bacteria | Nature | Number of experimental strains | Minimum inhibitory concentration MIC (μg/ml) |
|---|---|---|---|---|
| | (β-hemolytic *streptococcus*) | | | |
| | ★Erythromycin-resistant *S. pyogenes* | G+ | 11 | 8-16 |
| *Enterococcus* | *E. faecium* | G+ | 1 | 25 |
| | *E. faecalis* | G+ | 1 | 50 |
| *Neisseria* | *N. meningitidis* | G− | 1 | 6.25 |
| | *N. gonorrhoeae* | G− | 1 | 6.25 |
| *Escherichia* | *E. coli* ATCC25922 (standard strain) | G− | 1 | 6.25 |
| | *E. coli* (clinically isolated strain) | G− | 8 | 6.25-12.5 |
| | ★ATCC25922 (non-ESBLs-producing) | G− | 1 | 4 |
| | ★ATCC35218 (ESBLs-producing) | G− | 1 | 4 |
| | ★ESBLs-producing *E. coli* | G− | 10 | 4-8 |
| | ★non-ESBLs-producing *E. coli* | G− | 4 | 4-8 |
| | dysentery bacilli | G− | 1 | 6.5 |
| | *Salmonella* | G− | 1 | 12.5 |
| | *K. peneumoniae* | G− | 1 | 25 |
| | *K. oxytoca* | G− | 1 | 12.5 |
| | *Citrobacter* | G− | 1 | 12.5 |
| | *E. cloacae* | G− | 1 | 12.5 |
| | *S. fonticola* | G− | 1 | 12.5 |
| Anaerobic bacteria | *C. tetani* | G+ | 1 | 25 |
| | *C. perfrimgens* | G+ | 1 | 25 |
| | *Bacteroides fragilis* | G+ | 1 | 12.5 |
| *Corynebacterium* | *C. dipheriae* | G+ | 1 | 3.13 |
| | *C. acnes* | G+ | 1 | 3.13 |
| *Pseudomonas* | ★*P. aeruginosa* ATCC27853 (standard strain) | G− | 1 | 8 |
| | ★*P. aeruginosa* (IPM-S strain) | G− | 4 | 8-16 |
| | ★*P. aeruginosa* (IPM-R strain) | G− | 8 | 8-16 |
| *Acinetobacter* | *A. baumanii* (clinically isolated strain) | G− | 2 | 12.5 |
| *Bordetella* | *B. pertussis* | G− | 1 | 3.13 |
| *Haemophilus* | *H. influenzae* | G− | 1 | 3.13 |
| *Mycobacterium* | ★*M. tuberculosis* | G+ | 1 | 25 |

Note:
★indicates that the test result for the minimum inhibitory concentration was carried out by the third party.

Example 4: Preparation of the Ctryamp Polypeptide Antiseptic Formulations

1) Formulation: 0.01-1.5 g of the antiseptic polypeptide Ctryamp from *Chaerilus tryznai* Kovarik prepared in EXAMPLE 1, 5 g of glycerol, 7 g of hydroxypropylmethyl cellulose, 0.1 g of glycolic acid, 0.1 g of EDTA, added with sterilized water up to 100 g.

2) Preparation: The hydroxypropylmethylcellulose was sprayed onto the liquid surface (about 60 mL) to form a matrix for gel overnight, and then the matrix was de-foamed under vacuum after standing. The glycolic acid was mixed uniformly with other drug substances, and gradually added into slurry with mixing uniformly, during which vigorous agitation was avoided to prevent mixing of excess bubbles. It was subpackaged to obtain an antiseptic gel formulation.

3) Blank control gel formulation: The formulation had the same formulation and its preparation was the same as the above preparation, except containing no Ctryamp polypeptide.

Note that: HydroxypropylMethyl Cellulose (HPMC). Glycerol, Hydroxypropyl Methyl Cellulose, glycolic acid and EDTA were all of medicinal specifications.

Example 5: Inhibitory Effect of the Ctryamp Polypeptide Antiseptic Formulation on Standard *Escherichia coli*, *Staphylococcus Aureus*, MRSA and *Pseudomonas aeruginosa*

1) The finished gel formulation provided in EXAMPLE 4 was dissolved in sterilized normal saline at a ratio of 1:49, and was diluted with an equal ratio to 10 concentrations and placed in a 4° C. water tank.

2) The standard *Escherichia coli*, *Staphylococcus aureus*, MRSA and *Pseudomonas aeruginosa* were inoculated in LB medium with breed conservation, and cultured at 37° C. overnight.

3) The bacterial solution which had been cultured overnight was diluted to OD600=0.002 with fresh LB medium.

4) 80 μL of the above bacterial solution was added into each well in a 96-well plate.

5) 20 μL of the finished gel solution at different concentrations was added into the bacterial solution.

6) Negative control tests of the gel and normal saline as well as positive control tests of the raw material polypeptide and antibiotic were performed at the same time.

7) The 96-well plate was placed in an oscillator at 37° C. and 250 rpm to be cultured for 16 hours.

8) The 96-well plate was taken out after 16 hours, cooled to room temperature and placed onto a microplate reader to determine its absorbance at 630 nm.

9) The concentration of the solution completely without any light absorption was used as the minimum inhibitory concentration.

10) Antibacterial results showed that, the antiseptic formulation had potent inhibitory effect on the standard *Escherichia coli*, *Staphylococcus aureus*, MRSA and *Pseudomonas aeruginosa*. The formulation had a minimum inhibitory concentration MIC against *Escherichia coli, Staphylococcus aureus* of 6.25 µg/mL (calculated based on the active ingredient polypeptide in this formulation), thus had an identical minimum inhibitory concentration to the raw material polypeptide (the raw material Ctryamp and synthesized structurally homologous amphiphilic polypeptides thereof have a MIC against *Escherichia coli, Staphylococcus aureus* of 6.25 µg/mL). The formulation had a minimum inhibitory concentration MIC against MRSA of 6.25 µg/mL, and against *Pseudomonas aeruginosa* of 8 µg/mL (the raw material Ctryamp and synthesized structurally homologous amphiphilic polypeptides thereof have a MIC against MRSA and *Pseudomonas aeruginosa* of 6.25 µg/mL and 8 µg/mL, respectively). Whereas, the control formulation had no antiseptic activity.

Results of the antiseptic tests are shown in Table 4.

TABLE 4

The minimum inhibitory concentration (MIC) of Ctryamp polypeptide topical gel formulation from *Chaerilus tryznai* Kovarik against gram-negative, gram-positive bacteria and drug resistant bacteria

| Tested bacterial strain | Minimum inhibitory concentration MIC |
| --- | --- |
| *E. coli* | 6.25 |
| *E. coli* | 6.25 |
| *S. aureus* | 6.25 |
| *S. aureus* | 6.25 |
| Methicillin-resistant *S. aureus* (MRSA) | 6.25 |
| *P. aeruginosa* (clinically isolated strain) | 8 |
| *C. perfrimgens* | 25 |

Note:
Calculated based on the active ingredient, i.e., Ctryamp polypeptide or the structurally homologous polypeptides thereof in the formulation Example 6: A Clinical Trial of the Ctryamp Polypeptide Antiseptic Formulation on the Treatment of Patients with Wound Surface Bacterial Infections 1) General information of cases: in 82 patients in a treatment group, with 38 males and 44 females; aged from minimum 4 to maximum 76; disease classification: 28 cases with bruised wound surface, 12 cases with small-sized scald wound surface, 10 cases with residual burn wound surface, 12 cases with chronic ulcer affected by type 2 diabetic, 12 cases in perioperative period of a flap operation, and 8 cases after wide-range laser treatment for face. In 74 patients in a control group, with 36 males and 38 females; aged from minimum 5 to maximum 78; disease classification: 28 cases with bruised wound surface, 13 cases with small-sized scald wound surface, 10 cases with residual burn wound surface, 8 cases with chronic ulcer affected by type 2 diabetic, 10 cases in perioperative period of a flap operation, and 5 cases after laser treatment.

2) Treatment method in the experimental group: The topical Ctryamp polypeptide gel provided in EXAMPLE 4 (abbreviated as scorpion peptide antiseptic gel) was administered topically. All the wound or ulcer surfaces were applied with the scorpion peptide antiseptic gel to a thickness of about 1-2 mm, once every day; alternatively, the wound surfaces were covered with gauzes infiltrated with the scorpion peptide antiseptic gel, with drug replacement once every 3 days. Bruised wound surface and superficial II degree scald wound surface were all rinsed with 3% hydrogen peroxide solution, followed with sterilized normal saline until the wound surface was clean. After the necrotic tissues were removed, the wound surface was rinsed with sterilized normal saline again and surrounding skin was disinfected with 0.2% povidone iodine. After the wound surface was dried with sterile cotton balls, the scorpion peptide antiseptic gel was evenly coated onto the wound surface in a thickness of about 1-2 mm. Samples from the residual burn wound surface and chronic ulcer affected by type 2 diabetic were taken for bacterial culture, in order to observe the wound surface infections. After the wound surface was cleaned using the abovementioned method, the scorpion peptide antiseptic gel was coated evenly onto the wound surface. When granulation tissues have grown, skin was grafted punctiformly and then coated evenly with the scorpion peptide antiseptic gel in a thickness of about 1-2 mm, then covered with mesh gauzes and dressed under pressure, with the first dressing replacement in 3 days. For patients with chronic diabetes, long-term blood glucose was monitored to achieve near normal level, best with the Fasting plasma glucose (FPG) below 8 mmol/L. During the perioperative period of a flap operation, after the wound was cleaned, the scorpion peptide antiseptic gel was directly coated onto the wound surface for protection in a thickness of 1-2 mm. For the laser treatment, the wound surface was washed with normal saline and then directly coated with the scorpion peptide antiseptic gel in a thickness of 1-2 mm.

3) Treatment method in the control group: All the wounds or ulcer surfaces were cleaned, dressed with gauzes and treated with semi-exposure after 3 days while keeping the wound surfaces dry.

4) Efficacy results and comparison: 82 patients in the treatment group experienced surface healing in the first phase, without any infections and delayed healing of the wound surface, and without any allergic reactions or other adverse reactions. Efficacy was determined in accordance with the Antibacterial Drug Clinical Trial Guiding Principles issued by the National Ministry of Health in 2007. Results showed that in the 82 cases of the treatment group, 80 cases were significantly effective and 2 cases were effective, giving an effective rate of 100%. In the 74 cases of the control group, 50 cases were significantly effective, 20 cases were effective and 4 cases were ineffective, giving an effective rate of 95%. Statistical F-test for the two groups showed $P<0.05$. Comparison of the time for promotion of wound surface healing in both the groups is shown in Table 1. Statistical F-test showed $P<0.05$ (Table 5). Clinical treatment results showed that the topical gel provided in the present invention can effectively prevent and treat bacterial infections, and meanwhile can significantly promote wound repair and healing. The scorpion peptide antiseptic gel had potent bacterial inhibitory effect on MRSA and imipenem-resistant *Pseudomonas aeruginosa* (IPM-R strain), and had an uniquely efficient treatment for the superficial chronic refractory infection wound surface (in the 82 cases of the treatment group, 8 cases of bacterial cultures were infected with MRSA and 5 cases were infected with *Pseudomonas aeruginosa* IPM-R strains, which were both effectively treated with the scorpion peptide antiseptic gel).

TABLE 5

Average healing time of scorpion peptide antiseptic gel and conventional dressing change and comparisons therebetween*

| Group | Cases | Healing time (days) | Average healing time (days) |
|---|---|---|---|
| Scorpion peptide antiseptic gel | 82 | 5-20 | 12.14 ± 2.96 |
| Conventional dressing change | 74 | 7-28 | 18.85 ± 2.78 |

*For comparison between the two groups, P < 0.05.

Example 7: Clinical Trials of the Polypeptide Antiseptic Formulations on the Treatment of Patients with Acne 1) Case selection: The selected patients were all from Dermatology Clinic in People's Hospital of Wuhan University, which were acne patients confirmed clinically. Ones who had an allergic history to clindamycin or quinolones, had taken other anti-acne drugs in 15 days, and suffered from serious severe hepatic and renal dysfunction, as well as pregnant women and lactating women were excluded.

2) Groups of experiments: 258 patients were divided into an experimental group and a control group by using multi-center and open parallel control observation. Experimental group: 168 cases, with 76 males and 92 females, aged from 20 to 38. Control group: 90 cases, with 46 males and 44 females, aged from 22 to 39. The experimental group and control group were comparable in that there was no significant difference in various index values such as the age, sex, stage of disease and degree of skin damages between them.

3) Experimental method: The experimental group was topically administered with the medicament for treating acne of the topical Ctryamp polypeptide gel as provided in EXAMPLE 4. The control group was topically administered with 5% Sulfur Cream (prepared in the Drug manufacturing room in People's Hospital of Wuhan University). Administration method: The face was washed with warm water and liquid soap or sulfur soap to completely remove the facial oil and dirty. Then the medicament was dipped with a finger to be gently coated onto the wound repeatedly, once each morning and evening, with one course of treatment being continuous 2 weeks.

4) Efficacy observation and judgment criterion: 258 participators were visited once every week, and during return visit, tables for observation were filled in detail to record the number, change and adverse reaction of skin damages in facial acne of the patients. The efficacy statistics were based on the total percentage of reduction of various damages (comedo, inflammatory scars, abscesses, nodules, cystides) in acne. Healing: 100% of extinction of skin damages; significant: 76-99% of extinction of skin damages; effective: 50-70% of extinction of skin damages; ineffective: <50% of extinction of skin damages. At the end of the course of treatment, acne percentage after the treatment was calculated by a metering method to evaluate the efficacy. Meanwhile, adverse reactions were observed to determine whether there was local stimulation and systemic symptoms, and for a part of patients, examinations on routine blood and urine, and liver and kidney function were performed before and after the clinical trials 5) Statistical analysis compared with the control: In the 168 cases of the experimental group, 112 cases were healed, accounting for 66.7%; 51 cases were significant, accounting for 30.4%; 5 cases were effective, accounting for 2.98%; no case was ineffective, accounting for 0%, with a total effective rate of 100%. In the 90 cases of the control group, 5 cases were healed, accounting for 5.6%; 14 cases were significant, accounting for 15.6%; 20 cases were effective, accounting for 22.2%; and 51 cases were ineffective, accounting for 4%, with a total effective rate of 43%. By analyzing the efficiency, there was significant difference between the experimental group and control group, suggesting the efficacy on acne treatment in the experimental group is superior to the control group.

6) Adverse reactions: There was no adverse reaction in any of the 168 patients in the experimental group. Of the 90 patients in the control group, 5 cases had local burning sensation and flushing, which were self relieved after stopping drug administration without any treatment. In addition, in the experimental group, totally, the routine blood and urine in 10 cases, liver function in 16 cases and kidney function in 8 cases were examined before and after the treatment, no abnormal change was observed.

Example 8: Clinical Trials of the Ctryamp Polypeptide Antiseptic Formulation on the Treatment of Patients with Eczema 22 patients with chronic eczema were treated with the topical polypeptide antiseptic gel formulation as provided in EXAMPLE 4 in the Burn and Plastic Surgery Unit of the People's Hospital of Hubei Province, once every day. 19 cases in the control group were treated with 1% hydrocortisone cream externally, twice every day. The clinical observation time was 2 weeks. Experimental results showed that, the scorpion peptide antiseptic gel had unique curative effect on eczema with a curative rate of 100%, and with no relapse during clinical follow-up visits; whereas in the control group, clinical symptoms were reduced but there were severe relapses during follow-up visits.

Example 9: Bacteriostasis Experiment on Ctryamp Polypeptide Mutants

Experimental Materials:

Ctryamp polypeptide mutants: Each Ctryamp polypeptide mutant has the amino acid sequence as set forth in SEQ ID NOs: 21 to 52 in the SEQUENCE LISTING and the mutation type thereof is shown in Table 6. All these Ctryamp polypeptide mutants were synthesized by GL Biochem Ltd.

Standard strains: *Staphylococcus aureus* (RA) ATCC25923 and *Escherichia coli* (*E. coli*) ATCC25922; ampicillin (Amp).

MH medium: beef powder 2.0 g, soluble starch 1.5 g, acid hydrolyzed casein 17.5 g, pure water 1 L. The MH medium was autoclaved at 121° C. for 20 min for use.

Experimental Method:

(1) Inoculation: 10 µL of standard strains of *Staphylococcus aureus* (RA) ATCC25923 and *Escherichia coli* (*E. coli*) ATCC25922 were inoculated into 10 mL MH medium respectively and cultured overnight for 16 hours at 37° C. and 250 rpm.

(2) Transferred inoculation: 100 µL resulted bacterial solutions of the standard strains of *Staphylococcus aureus* (RA) ATCC25923 and *Escherichia coli* (*E. coli*) ATCC25922 cultured overnight were transferred respectively into 10 mL of fresh MH medium and cultured at 37° C. and 250 rpm for 2 hours.

(3) Dilution of bacterial solution: The bacterial solutions of the standard strains of *Staphylococcus aureus* (RA) ATCC25923 and *Escherichia coli* (*E. coli*) ATCC25922 obtained in (2) were taken separately to determine their OD$_{600}$ values, they were diluted with MH medium to OD$_{600}$=0.002 respectively.

(4) Sample application: 100 μL of MH medium was added into the periphery of a sterile 96-well plate as a guard circle; each well inside the guard circle was added with 80 μL of the diluted bacterial solution obtained in step (3); and then the wells with the bacterial solution inside the guard circle were added with 20 μL of a formulated solution of the Ctryamp polypeptide mutants, with a sequence ranging from a low concentration to a high concentration, each concentration was repeated in 3 wells. 20 μL of 20 mg/mL ampicillin was used as a positive control and 20 μL of sterile water was used as a negative control.

(5) Culture: The 96-well plated obtained in step (4) was placed on an oscillator at 37° C. and 250 rpm for 16 hours.

(6) Detection: After cultured for 16 hours, the 96-well plate was taken out to observe the bacterial growth therein and record experimental results, with the corresponding sample concentration (concentration of the Ctryamp polypeptide mutant) in a well where there was no bacterial growth as a minimum inhibitory concentration (MIC) against the bacterium.

Experimental Results:

Experimental results of the inhibitory effect of each Ctryamp polypeptide mutant on the standard strains of *Staphylococcus aureus* (RA) ATCC25923 and *Escherichia coli* (*E. coli*) ATCC25922 are shown in Table 7.

TABLE 6

The information of the amino acid sequences of Ctryamp polypeptide mutants and mutation types

| Ctryamp polypeptide mutant | Amino acid sequence | Position in Sequence Listing | Mutation type |
|---|---|---|---|
| Ctryamp polypeptide mutant 1 | FIRIARLLEIF | SEQ ID NO: 21 | Single-point mutation (substitution) |
| Ctryamp polypeptide mutant 2 | FIRIADLLRIF | SEQ ID NO: 22 | Single-point mutation (substitution) |
| Ctryamp polypeptide mutant 3 | FIRIAKLLKIF | SEQ ID NO: 23 | Two-point mutation (substituted) |
| Ctryamp polypeptide mutant 4 | FIKIARLLKIF | SEQ ID NO: 24 | Two-point mutation (substituted) |
| Ctryamp polypeptide mutant 5 | FIKIAKLLKIF | SEQ ID NO: 25 | Three-point mutation (substituted) |
| Ctryamp polypeptide mutant 6 | FIKIGKLLKIF | SEQ ID NO: 26 | Four-point mutation (substituted) |
| Ctryamp polypeptide mutant 7 | FIKIGKILKIF | SEQ ID NO: 27 | Five-point mutation (substituted) |
| Ctryamp polypeptide mutant 8 | FIRIARLRIF | SEQ ID NO: 28 | 1 amino acid deleted |
| Ctryamp polypeptide mutant 9 | FRIARLLRIF | SEQ ID NO: 29 | 1 amino acid deleted |
| Ctryamp polypeptide mutant 10 | FIRARLLRIF | SEQ ID NO: 30 | 1 amino acid deleted |
| Ctryamp polypeptide mutant 11 | FIRIARLLIF | SEQ ID NO: 31 | 1 amino acid deleted |
| Ctryamp polypeptide mutant 12 | FIRRLLRIF | SEQ ID NO: 32 | 2 amino acids deleted |
| Ctryamp polypeptide mutant 13 | FIRRLRIF | SEQ ID NO: 33 | 3 amino acids deleted |
| Ctryamp polypeptide mutant 14 | FIRLRIF | SEQ ID NO: 34 | 4 amino acids deleted |
| Ctryamp polypeptide mutant 15 | RLLRIF | SEQ ID NO: 35 | 5 amino acids deleted |
| Ctryamp polypeptide mutant 16 | GFIRIARLLRIF | SEQ ID NO: 36 | 1 amino acid added |
| Ctryamp polypeptide mutant 17 | FIRIARLLRKIF | SEQ ID NO: 37 | 1 amino acid added |
| Ctryamp polypeptide mutant 18 | FIRIARLLKRIF | SEQ ID NO: 38 | 1 amino acid added |

TABLE 6-continued

The information of the amino acid sequences of Ctryamp polypeptide mutants and mutation types

| Ctryamp polypeptide mutant | Amino acid sequence | Position in Sequence Listing | Mutation type |
|---|---|---|---|
| Ctryamp polypeptide mutant 19 | FIRKIARLLRIF | SEQ ID NO: 39 | 1 amino acid added |
| Ctryamp polypeptide mutant 20 | FIKRIARLLRIF | SEQ ID NO: 40 | 1 amino acid added |
| Ctryamp polypeptide mutant 21 | FFIRIARLLRIF | SEQ ID NO: 41 | 1 amino acid added |
| Ctryamp polypeptide mutant 22 | IFFIRIARLLRIF | SEQ ID NO: 42 | 2 amino acids added |
| Ctryamp polypeptide mutant 23 | RIFFIRIARLLRIF | SEQ ID NO: 43 | 3 amino acids added |
| Ctryamp polypeptide mutant 24 | LRIFFIRIARLLRIF | SEQ ID NO: 44 | 4 amino acids added |
| Ctryamp polypeptide mutant 25 | LLRIFFIRIARLLRIF | SEQ ID NO: 45 | 5 amino acids added |
| Ctryamp polypeptide mutant 26 | RLLRIFFIRIARLLRIF | SEQ ID NO: 46 | 6 amino acids added |
| Ctryamp polypeptide mutant 27 | ARLLRIFFIRIARLLRIF | SEQ ID NO: 47 | 7 amino acids added |
| Ctryamp polypeptide mutant 28 | IARLLRIFFIRIARLLRIF | SEQ ID NO: 48 | 8 amino acids added |
| Ctryamp polypeptide mutant 29 | RIARLLRIFFIRIARLLRIF | SEQ ID NO: 49 | 9 amino acids added |
| Ctryamp polypeptide mutant 30 | IRIARLLRIFFIRIARLLRIF | SEQ ID NO: 50 | 10 amino acids added |
| Ctryamp polypeptide mutant 31 | FIRIARLLRIFFIRIARLLRIF | SEQ ID NO: 51 | 11 amino acids added |
| Ctryamp polypeptide mutant 32 | Ac-FIRIARLLRIF | SEQ ID NO: 52 | Acetylation of Phe residue at N terminal |

Note:
The amino acid sequence "Ac-FIRIARLLRIF" which the Ctryamp polypeptide mutant 32 corresponds to represents that the amino group on Phe residue at the N terminal of "FIRIARLLRIF" is modified with an acetyl group.

Note: The amino acid sequence "Ac-FIRIARLLRIF" (SEQ ID NO: 52) which the Ctryamp polypeptide mutant 32 corresponds to represents that the amino group on Phe residue at the N terminal of "FIRIARLLRIF" (SEQ ID NO: 2) is modified with an acetyl group.

TABLE 7

Minimum inhibitory concentration of Ctryamp polypeptide mutant against standard strains of *Staphylococcus aureus* (RA) ATCC25923 and *Escherichia coli* (E. coli) ATCC25922

| | MIC (µg/mL) | |
|---|---|---|
| Ctryamp polypeptide mutant | *Staphylococcus aureus* (RA) ATCC25923 | *Escherichia coli* (E. Coli) ATCC25922 |
| Ctryamp polypeptide mutant 1 | >25 | >25 |
| Ctryamp polypeptide mutant 2 | 25 | >25 |
| Ctryamp polypeptide mutant 3 | 12.5 | 12.5 |
| Ctryamp polypeptide mutant 4 | 12.5 | 12.5 |
| Ctryamp polypeptide mutant 5 | 25 | 12.5 |
| Ctryamp polypeptide mutant 6 | 25 | 12.5 |
| Ctryamp polypeptide mutant 7 | >25 | 12.5 |
| Ctryamp polypeptide mutant 8 | 25 | 12.5 |
| Ctryamp polypeptide mutant 9 | 12.5 | 6.25 |
| Ctryamp polypeptide mutant 10 | >25 | >25 |
| Ctryamp polypeptide mutant 11 | >25 | >25 |
| Ctryamp polypeptide mutant 12 | 12.5 | 25 |
| Ctryamp polypeptide mutant 13 | >25 | >25 |
| Ctryamp polypeptide mutant 14 | >25 | >25 |
| Ctryamp polypeptide mutant 15 | >25 | >25 |
| Ctryamp polypeptide mutant 16 | 6.25 | 6.25 |
| Ctryamp polypeptide mutant 17 | 6.25 | 12.5 |

TABLE 7-continued

Minimum inhibitory concentration of Ctryamp polypeptide mutant against standard strains of *Staphylococcus aureus* (*RA*) *ATCC25923 and Escherichia coli* (*E. coli*) ATCC25922

| Ctryamp polypeptide mutant | MIC (μg/mL) | |
|---|---|---|
| | *Staphylococcus aureus* (RA) ATCC25923 | *Escherichia coli* (*E. Coli*) ATCC25922 |
| Ctryamp polypeptide mutant 18 | 6.25 | 12.5 |
| Ctryamp polypeptide mutant 19 | 6.25 | 6.25 |
| Ctryamp polypeptide mutant 20 | 6.25 | 6.25 |
| Ctryamp polypeptide mutant 21 | 12.5 | 25 |
| Ctryamp polypeptide mutant 22 | 12.5 | >25 |
| Ctryamp polypeptide mutant 23 | 12.5 | 12.5 |
| Ctryamp polypeptide mutant 24 | 25 | >25 |
| Ctryamp polypeptide mutant 25 | 25 | >25 |
| Ctryamp polypeptide mutant 26 | >25 | >25 |
| Ctryamp polypeptide mutant 27 | >25 | >25 |
| Ctryamp polypeptide mutant 28 | >25 | >25 |
| Ctryamp polypeptide mutant 29 | >25 | >25 |
| Ctryamp polypeptide mutant 30 | >25 | >25 |
| Ctryamp polypeptide mutant 31 | >25 | >25 |
| Ctryamp polypeptide mutant 32 | 6.25 | 25 |

Note:
MIC > 25 μg/mL of the Ctryamp polypeptide mutant indicates MIC is greater than or equal to 50 μg/mL, and indicates weak or no antiseptic activity, that is, no clinical application value.

From the experimental results in Table 7, the Ctryamp polypeptide mutants 2 to 9, 12, 16 to 25 and 32 all had significant inhibitory effect against *Staphylococcus aureus* (RA) ATCC25923 and/or *Escherichia coli* (*E. coli*) ATCC25922. The Ctryamp polypeptide mutants 1, 10, 11, 13, 14, 15 and 26 to 31 had weak (MIC>25 μg/mL) or no inhibitory activity against *Staphylococcus aureus* and *Escherichia coli.*

The experimental results indicate that, after the polypeptide having the amino acid sequence as set forth in SEQ ID NO: 1 is subjected to the substitution, deletion, addition or modification of one or more amino acids, some still have biological activity while some have weak or no antiseptic activity.

For the Ctryamp polypeptide mutants remaining the antiseptic activity, when the polypeptide having the amino acid sequence as set forth in SEQ ID NO: 1 was subjected to the substitution of 1, 2, 3, 4 or 5 amino acids and the number of the substitution amino acid is 1, the polypeptides not having the amino acid sequence of SEQ ID NO: 21 would still have the antiseptic activity; when the polypeptide having the amino acid sequence as set forth in SEQ ID NO: 1 was subjected to the deletion of 1 or 2 amino acids, and when 1 amino acid was deleted, the deleted amino acid residue is not at position 4 or 9, the polypeptides not having the amino acid sequence of SEQ ID NO: 30 or SEQ ID NO: 31 would still have the antiseptic activity; when the polypeptide having the amino acid sequence as set forth in SEQ ID NO: 1 was subjected to the addition of 1-5 amino acids at its N terminal, the polypeptides would still have the antiseptic activity; and after the Ctryamp polypeptide mutants were subjected to the modification of amidation, phosphorylation, methylation, acetylation, ubiquitination, glycosylation or carbonylation, the polypeptides would still have the antiseptic activity; for example, when the Phe residue at the N terminal of the Ctryamp polypeptide was modified with acetylation, the formed mutant 32 having the amino acid sequence as set forth in SEQ ID NO: 52 would still have the antiseptic activity.

For the Ctryamp polypeptide mutants having weak or no antiseptic activity, when the amino acid sequence as set forth in SEQ ID NO: 1 was substituted with a single amino acid, the polypeptide having the amino acid sequence as set forth in SEQ ID NO: 21 had no antiseptic activity. When the amino acid sequence as set forth in SEQ ID NO: 1 was deleted with 3, 4 or 5 amino acids, the biological activity thereof would be influenced. When the polypeptide was deleted with a single amino acid, the deleted amino acid residue should not be at position 4 or 9, and the polypeptide should not have the amino acid sequence as set forth in SEQ ID NO: 30 or SEQ ID NO: 31. When the polypeptide having the amino acid sequence as set forth in SEQ ID NO: 1 was added with 6-11 amino acids at its N terminal, the biological activity thereof would be influenced.

Comparative Example 1: Inhibitory Activity of Existing Polypeptides

The polypeptides of amino acid sequences as set forth in SEQ ID NO: 2 and SEQ ID NO: 4, SEQ ID NO: 5, SEQ ID NO: 6 were compared for their antiseptic activity, and the results are shown in Table 8. It was found that although all these 4 polypeptides could effectively inhibit *Staphylococcus aureus*, ABP-W1 (SEQ ID NO: 4) and BmKAMP1 (SEQ ID NO: 5) had no inhibitory effect on gram-negative bacteria (MIC was 50 μg/mL), such as *Escherichia coli, Pseudomonas aeruginosa* and the like. The BmKAMP1-M (SEQ ID NO: 6) had relatively good inhibitory effect on *Escherichia coli* but had poor inhibitory effect on clinically common *Pseudomonas aeruginosa* (MIC was 50 μg/mL), which did not have any clinical application value. However, the Ctryamp polypeptide (SEQ ID NO: 2) had the broadest antiseptic spectrum. It not only had strong antiseptic activity against *Staphylococcus aureus, Escherichia coli* and *Pseudomonas aeruginosa*, but also had high antiseptic activity against several gram-negative bacteria, gram-positive bacteria and specific infection pathogenic bacteria. This showed a significantly different clinical application value from SEQ ID NO: 4, SEQ ID NO: 5 and SEQ ID NO: 6. Meanwhile, it was also found in the present invention that, the Ctryamp polypeptide (SEQ ID NO: 2) also had unique curative effect on eczema.

It follows that, the polypeptide having the amino acid sequence as set forth in SEQ ID NO: 1, as well as the derived polypeptides having the amino acid sequences obtained by the modification, substitution, deletion or addition of one or more amino acids to the sequence of SEQ ID NO: 1, have the properties of high antiseptic activity and broad antiseptic spectrum. They have inhibitory effect with high activity on various bacteria (pathogenic bacteria) and also have uniquely effective effect on the prevention and treatment of infections caused by gram-positive bacteria, gran-negative bacteria and various drug resistant bacteria, and on the prevention and treatment of specific infections (infectious diseases) caused by specific pathogenic bacteria and eczema.

TABLE 8

Comparison of minimum inhibitory concentration for existing polypeptides

| Bacteria name | Minimum inhibitory concentration MIC (μg/mL) | | | |
| --- | --- | --- | --- | --- |
| | Ctryamp (SEQ ID NO: 2) | ABP-W1 (SEQ ID NO: 4) | BmKAMP1 (SEQ ID NO: 5) | BmKAMP1-M (SEQ ID NO: 6) |
| Staphylococcus aureus (methicillin-sensitive) | 1.63-6.25 | 3.13 | 3.13 | 12.5 |
| Methicillin-resistant Staphylococcus aureus | 6.25 | 8 | 12.5 | 6.25 |
| Escherichia coli | 6.25 | >100 | >100 | 12.5 |
| Pseudomonas aeruginosa | 8 | >100 | >100 | 50 |
| Corynebacterium diphtheriae | 3.13 | / | / | / |
| Acinetobacter baumannii | 12.5 | / | / | / |
| Klebsiella pneumoniae | 25 | / | / | / |
| Serratia fonticola | 12.5 | / | / | / |
| Clostridium perfringens | 25 | / | / | / |
| Salmonella | 12.5 | / | / | / |
| Shigella | 6.25 | / | / | / |
| Citrobacter | 12.5 | / | / | / |
| Klebsiella oxytoca | 12.5 | / | / | / |
| Bordetella pertussis | 3.13 | / | / | / |
| Streptococcus pneumoniae | 3.13 | / | / | / |
| Enterococcus faecium | 25 | / | / | / |
| Streptococcus agalactiae | 25 | / | / | / |
| Enterobacter cloacae | 12.5 | / | / | / |
| Neisseria meningitidis | 6.25 | / | / | / |
| Neisseria gonorrhoeae | 6.25 | / | / | / |
| Clostridium tetani | 25 | / | / | / |
| Corynebacterium acnes | 3.13 | / | / | / |
| Haemophilus influenzae | 3.13 | / | / | / |
| Mycobacterium tuberculosis | 25 | / | / | / |

"/" indicates it is not found.

The foregoing are only preferred modes of the present invention, and it is to be indicated that, for those skilled in the art, various improvements and modifications can be made without departing from the principles of the present invention, which shall be also deemed to fall within the protection scope of the present invention.

The invention claimed is:

1. A method for the improvement of condition in a subject comprising administering a polypeptide to the subject,
wherein the polypeptide has any one of the amino acid sequences of (I) and (II):
(I) the amino acid sequence of SEQ ID NO: 1;
(II) amino acid sequences obtained from the amino acid sequence as set forth in SEQ ID NO: 1 with amidation, phosphorylation, methylation, acetylation, ubiquitination, or carbonylation of one or more amino acids, and
wherein the improvement of condition is selected from the group consisting of:
the inhibition of bacteria;
the prevention and/or treatment of a bacterial infection disease and/or eczema;
the promotion of tissue repair and/or wound healing; and
the treatment of a burn injury, cold injury, crush injury, war injury, animal bite, nuclear radiation injury or combined injury.

2. The method of claim 1, wherein the bacterium is a Gram-positive bacterium and/or a Gram-negative bacterium.

3. The method of claim 1, wherein the Gram-positive bacterium belongs to *Staphylococcus, Streptococcus, Enterococcus, Mycobacterium*, anaerobic bacterium and/or *Corynebacterium*; and/or the Gram-negative bacterium belongs to *Neisseria, Enterobacteriaceae, Pseudomonas, Acinetobacter, Bordetella* and/or *Haemophilus*.

4. The method of claim 1, wherein the infection is a nonspecific infection and/or specific infection.

5. The method of claim 4, wherein the nonspecific infection is furuncle, carbuncle, erysipelas, acute lymphangitis, acute lymphadenitis, paronychia, felon, lateral pyogenic tenosynovitis of fingers, bursitis, palm deep space infection, pyemia or bacteremia; and/or the specific infection is tuberculosis, tetanus, gas gangrene, anthrax, pertussis, epidemic encephalomyelitis, gonorrhea, typhia, bacillary dysentery or diphtheria.

6. The method of claim 1, wherein the infection is an infection caused by MRSA, MRCNS, erythromycin-resistant *Streptococcus pyogenes*, ESBL-producing *Escherichia coli*, imipenem-resistant *Pseudomonas aeruginosa*; or
the infection is a local infection, systemic infection or toxic disease caused by *Staphylococcus aureus*; or
the infection is a urinary system infection, septicemia or postoperative infection, caused by coagulase-negative *Staphylococcus*; or
the infection is a pyogenic inflammation, rheumatic fever, acute glomerulonephritis, scarlatina, bacterial pneumonia, saprodontia, subacute bacterial endocarditis or newborn infection, caused by *Streptococcus*; or the infection is lobar pneumonia, trachitis, otitis media, meningitis, pleurisy, endocarditis or septicemia, caused by *Streptococcus pneumonia*; or
the infection is puerperal septicopyemia in pregnant women, neonatal meningitis, postpartum infection, bacteremia, endocarditis, skin infection, soft tissue infection or osteomyelitis, caused by *Streptococcus agalactiae*; or
the infection is a cardiovascular system infection or urinary tract infection, caused by *Enterococcus*; or
the infection is a urinary tract infection, pyogenic abdominal infection, septicemia, endocarditis or diarrhea fever, caused by *Enterococcus faecium*; or
the infection is endocarditis, cholecystitis, meningitis, urinary tract infection or wound infection, caused by *Enterococcus faecalis*; or
the infection is epidemic encephalomyelitis caused by *Neisseria meningitides*; or
the infection is gonorrhea caused by *Neisseria gonorrhoeae*; or
the infection is a urinary system infection, parenteral pyogenic infection, intestinal infection or hemorrhagic colitis, caused by *Escherichia*; or
the infection is bacillary dysentery caused by *Shigella*; or
the infection is typhia and paratyphoid caused by *Salmonella*; or
the infection is pneumonia, bronchitis, urinary tract infection, wound infection, meningitis or peritonitis, caused by *Klebsiella pneumonia*; or
the infection is antibiotic-associated hemorrhagic colitis caused by *Klebsiella oxytoca*; or
the infection is pneumonia or meningitis caused by *Citrobacter*; or
the infection is skin infection, soft tissue infection, urinary tract infection, respiratory tract infection, abdominal infection, central nervous system infection, eye infection, wound infection, endocarditis or septicemia, caused by *Enterobacter cloacae*; or
the infection is pneumonia, urinary tract infection, bacteremia or postoperative infection, caused by *Serratia*; or
the infection is tetanus caused by *Clostridium tetani*; or
the infection is gas gangrene or food poisoning caused by *Clostridium perfringens*; or
the infection is abdominal infection, female reproductive tract and pelvic infection or bacteremia, caused by asporous anaerobic bacterium; or
the infection is diphtheria caused by *Corynebacterium diphtheria*; or
the infection is acne or comedo caused by *Corynebacterium acnes*; or the infection is a wound infection, burn tissue infection, lung infection, urinary tract infection, otitis media, keratitis, endocarditis or septicemia, caused by *Pseudomonas aeruginosa*; or the infection is a respiratory tract infection, bacteremia, urinary tract infection, secondary meningitis, surgical site infection or ventilator-associated pneumonia, caused by *Acinetobacter baumannii*; or the infection is pertussis caused by *Bordetella pertussis*; or the infection is bacteremia in infants or children, acute bacterial meningitis, cellulitis, osteomyelitis or joint infection, caused by *Haemophilus*; or such as *Haemophilus* influenza; or the infection is tuberculosis caused by *Mycobacterium tuberculosis*; or the infection is a chronic refractory infection of a wound surface.

\* \* \* \* \*

```
                    SEQUENCE LISTING

<160> NUMBER OF SEQ ID NOS: 71

<210> SEQ ID NO 1
<211> LENGTH: 11
<212> TYPE: PRT
<213> ORGANISM: Artificial Sequence
<220> FEATURE:
<223> OTHER INFORMATION: Synthesized Ctryamp polypeptide
<220> FEATURE:
<221> NAME/KEY: VARIANT
<222> LOCATION: (1)..(11)
<223> OTHER INFORMATION: Xaa(3)=His,Arg or Lys;Xaa(6)=His,Arg or
      Lys;Xaa(9)=His,Arg or Lys.

<400> SEQUENCE: 1

Phe Ile Xaa Ile Ala Xaa Leu Leu Xaa Ile Phe
1               5                   10

<210> SEQ ID NO 2
<211> LENGTH: 11
<212> TYPE: PRT
<213> ORGANISM: Chaerilus tryznai Kovarik

<400> SEQUENCE: 2

Phe Ile Arg Ile Ala Arg Leu Leu Arg Ile Phe
1               5                   10

<210> SEQ ID NO 3
```

```
<211> LENGTH: 325
<212> TYPE: DNA
<213> ORGANISM: Chaerilus tryznai Kovarik

<400> SEQUENCE: 3
ttcctctgtg aaagtaagtt ctgtgaaact cactcttcga taaaatgaaa tctcagacct      60
ttttccttct ttttctagtt gttttattat tagcaatttc acaatcagaa gcttttatca     120
ggatcgccag gctcctcagg atctttggaa aaagaagtat gagagatatg gatactatga     180
aatacttata tgaaccaagt ttgagtgcag ctgacttgaa aaccttacaa aaactaatgg     240
aaaattactg attatttgaa tataataatg ttatctctat tttagattat aaatatttct     300
tttgaaaaaa aaaaaaaaaa aaaaa                                           325

<210> SEQ ID NO 4
<211> LENGTH: 13
<212> TYPE: PRT
<213> ORGANISM: Mesobuthus martensii karsch

<400> SEQUENCE: 4

Phe Ile Gly Ala Ile Ala Arg Leu Leu Arg Lys Ile Phe
1               5                   10

<210> SEQ ID NO 5
<211> LENGTH: 13
<212> TYPE: PRT
<213> ORGANISM: Mesobuthus martensii karsch

<400> SEQUENCE: 5

Phe Ile Gly Ala Ile Ala Arg Leu Leu Ser Lys Ile Phe
1               5                   10

<210> SEQ ID NO 6
<211> LENGTH: 13
<212> TYPE: PRT
<213> ORGANISM: Mesobuthus martensii karsch

<400> SEQUENCE: 6

Phe Ile Lys Arg Ile Ala Arg Leu Leu Arg Lys Ile Phe
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthesized Ctryamp polypeptide

<400> SEQUENCE: 7

Phe Ile Lys Ile Ala Arg Leu Leu Arg Ile Phe
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthesized Ctryamp polypeptide

<400> SEQUENCE: 8

Phe Ile Arg Ile Ala Lys Leu Leu Arg Ile Phe
1               5                   10

<210> SEQ ID NO 9
```

```
<211> LENGTH: 11
<212> TYPE: PRT
<213> ORGANISM: Artificial Sequence
<220> FEATURE:
<223> OTHER INFORMATION: Synthesized Ctryamp polypeptide

<400> SEQUENCE: 9

Phe Ile Arg Ile Ala Arg Leu Leu Lys Ile Phe
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthesized Ctryamp polypeptide

<400> SEQUENCE: 10

Phe Ile His Ile Ala Arg Leu Leu Arg Ile Phe
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Synthesized Ctryamp polypeptide

<400> SEQUENCE: 11

Phe Ile Arg Ile Ala His Leu Leu Arg Ile Phe
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthesized Ctryamp polypeptide

<400> SEQUENCE: 12

Phe Ile Arg Ile Ala Arg Leu Leu His Ile Phe
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthesized Ctryamp polypeptide

<400> SEQUENCE: 13

Phe Ile Lys Ile Ala Lys Leu Leu Arg Ile Phe
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Synthesized Ctryamp polypeptide

<400> SEQUENCE: 14

Phe Ile Lys Ile Ala Arg Leu Leu Lys Ile Phe
1               5                   10

<210> SEQ ID NO 15
<211> LENGTH: 11
```

```
<212> TYPE: PRT
<213> ORGANISM: Artificial Sequence
<220> FEATURE:
<223> OTHER INFORMATION: Synthesized Ctryamp polypeptide

<400> SEQUENCE: 15

Phe Ile Arg Ile Ala Lys Leu Leu Lys Ile Phe
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Synthesized Ctryamp polypeptide

<400> SEQUENCE: 16

Phe Ile Lys Ile Ala Lys Leu Leu Lys Ile Phe
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Synthesized Ctryamp polypeptide

<400> SEQUENCE: 17

Phe Ile His Ile Ala His Leu Leu Arg Ile Phe
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Synthesized Ctryamp polypeptide

<400> SEQUENCE: 18

Phe Ile His Ile Ala Arg Leu Leu His Ile Phe
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Synthesized Ctryamp polypeptide

<400> SEQUENCE: 19

Phe Ile His Ile Ala Lys Leu Leu Arg Ile Phe
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthesized Ctryamp polypeptide

<400> SEQUENCE: 20

Phe Ile Arg Ile Ala Lys Leu Leu His Ile Phe
1               5                   10

<210> SEQ ID NO 21
<211> LENGTH: 11
<212> TYPE: PRT
```

<213> ORGANISM: Artificial Sequence
<220> FEATURE:
<223> OTHER INFORMATION: Synthesized Ctryamp polypeptide

<400> SEQUENCE: 21

Phe Ile Arg Ile Ala Arg Leu Leu Glu Ile Phe
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Synthesized Ctryamp polypeptide

<400> SEQUENCE: 22

Phe Ile Arg Ile Ala Asp Leu Leu Arg Ile Phe
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Synthesized Ctryamp polypeptide

<400> SEQUENCE: 23

Phe Ile Arg Ile Ala Lys Leu Leu Lys Ile Phe
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Synthesized Ctryamp polypeptide

<400> SEQUENCE: 24

Phe Ile Lys Ile Ala Arg Leu Leu Lys Ile Phe
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Synthesized Ctryamp polypeptide

<400> SEQUENCE: 25

Phe Ile Lys Ile Ala Lys Leu Leu Lys Ile Phe
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Synthesized Ctryamp polypeptide

<400> SEQUENCE: 26

Phe Ile Lys Ile Gly Lys Leu Leu Lys Ile Phe
1               5                   10

<210> SEQ ID NO 27
<211> LENGTH: 11
<212> TYPE: PRT
<213> ORGANISM: Artificial Sequence

```
<220> FEATURE:
<223> OTHER INFORMATION: Synthesized Ctryamp polypeptide

<400> SEQUENCE: 27

Phe Ile Lys Ile Gly Lys Ile Leu Lys Ile Phe
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Synthesized Ctryamp polypeptide

<400> SEQUENCE: 28

Phe Ile Arg Ile Ala Arg Leu Arg Ile Phe
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Synthesized Ctryamp polypeptide

<400> SEQUENCE: 29

Phe Arg Ile Ala Arg Leu Leu Arg Ile Phe
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Synthesized Ctryamp polypeptide

<400> SEQUENCE: 30

Phe Ile Arg Ala Arg Leu Leu Arg Ile Phe
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Synthesized Ctryamp polypeptide

<400> SEQUENCE: 31

Phe Ile Arg Ile Ala Arg Leu Leu Ile Phe
1               5                   10

<210> SEQ ID NO 32
<211> LENGTH: 9
<212> TYPE: PRT
<213> ORGANISM: Artificial Sequence
<220> FEATURE:
<223> OTHER INFORMATION: Synthesized Ctryamp polypeptide

<400> SEQUENCE: 32

Phe Ile Arg Arg Leu Leu Arg Ile Phe
1               5

<210> SEQ ID NO 33
<211> LENGTH: 8
<212> TYPE: PRT
<213> ORGANISM: Artificial Sequence
<220> FEATURE:
```

<223> OTHER INFORMATION: Synthesized Ctryamp polypeptide

<400> SEQUENCE: 33

Phe Ile Arg Arg Leu Arg Ile Phe
1               5

<210> SEQ ID NO 34
<211> LENGTH: 7
<212> TYPE: PRT
<213> ORGANISM: Artificial Sequence
<220> FEATURE:
<223> OTHER INFORMATION: Synthesized Ctryamp polypeptide

<400> SEQUENCE: 34

Phe Ile Arg Leu Arg Ile Phe
1               5

<210> SEQ ID NO 35
<211> LENGTH: 6
<212> TYPE: PRT
<213> ORGANISM: Artificial Sequence
<220> FEATURE:
<223> OTHER INFORMATION: Synthesized Ctryamp polypeptide

<400> SEQUENCE: 35

Arg Leu Leu Arg Ile Phe
1               5

<210> SEQ ID NO 36
<211> LENGTH: 12
<212> TYPE: PRT
<213> ORGANISM: Artificial Sequence
<220> FEATURE:
<223> OTHER INFORMATION: Synthesized Ctryamp polypeptide

<400> SEQUENCE: 36

Gly Phe Ile Arg Ile Ala Arg Leu Leu Arg Ile Phe
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Synthesized Ctryamp polypeptide

<400> SEQUENCE: 37

Phe Ile Arg Ile Ala Arg Leu Leu Arg Lys Ile Phe
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Synthesized Ctryamp polypeptide

<400> SEQUENCE: 38

Phe Ile Arg Ile Ala Arg Leu Leu Lys Arg Ile Phe
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Synthesized Ctryamp polypeptide

<400> SEQUENCE: 39

Phe Ile Arg Lys Ile Ala Arg Leu Leu Arg Ile Phe
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Synthesized Ctryamp polypeptide

<400> SEQUENCE: 40

Phe Ile Lys Arg Ile Ala Arg Leu Leu Arg Ile Phe
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Synthesized Ctryamp polypeptide

<400> SEQUENCE: 41

Phe Phe Ile Arg Ile Ala Arg Leu Leu Arg Ile Phe
1               5                   10

<210> SEQ ID NO 42
<211> LENGTH: 13
<212> TYPE: PRT
<213> ORGANISM: Artificial Sequence
<220> FEATURE:
<223> OTHER INFORMATION: Synthesized Ctryamp polypeptide

<400> SEQUENCE: 42

Ile Phe Phe Ile Arg Ile Ala Arg Leu Leu Arg Ile Phe
1               5                   10

<210> SEQ ID NO 43
<211> LENGTH: 14
<212> TYPE: PRT
<213> ORGANISM: Artificial Sequence
<220> FEATURE:
<223> OTHER INFORMATION: Synthesized Ctryamp polypeptide

<400> SEQUENCE: 43

Arg Ile Phe Phe Ile Arg Ile Ala Arg Leu Leu Arg Ile Phe
1               5                   10

<210> SEQ ID NO 44
<211> LENGTH: 15
<212> TYPE: PRT
<213> ORGANISM: Artificial Sequence
<220> FEATURE:
<223> OTHER INFORMATION: Synthesized Ctryamp polypeptide

<400> SEQUENCE: 44

Leu Arg Ile Phe Phe Ile Arg Ile Ala Arg Leu Leu Arg Ile Phe
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: Synthesized Ctryamp polypeptide

```
<400> SEQUENCE: 45

Leu Leu Arg Ile Phe Phe Ile Arg Ile Ala Arg Leu Leu Arg Ile Phe
1               5                   10                  15

<210> SEQ ID NO 46
<211> LENGTH: 17
<212> TYPE: PRT
<213> ORGANISM: Artificial Sequence
<220> FEATURE:
<223> OTHER INFORMATION: Synthesized Ctryamp polypeptide

<400> SEQUENCE: 46

Arg Leu Leu Arg Ile Phe Phe Ile Arg Ile Ala Arg Leu Leu Arg Ile
1               5                   10                  15

Phe

<210> SEQ ID NO 47
<211> LENGTH: 18
<212> TYPE: PRT
<213> ORGANISM: Artificial Sequence
<220> FEATURE:
<223> OTHER INFORMATION: Synthesized Ctryamp polypeptide

<400> SEQUENCE: 47

Ala Arg Leu Leu Arg Ile Phe Phe Ile Arg Ile Ala Arg Leu Leu Arg
1               5                   10                  15

Ile Phe

<210> SEQ ID NO 48
<211> LENGTH: 19
<212> TYPE: PRT
<213> ORGANISM: Artificial Sequence
<220> FEATURE:
<223> OTHER INFORMATION: Synthesized Ctryamp polypeptide

<400> SEQUENCE: 48

Ile Ala Arg Leu Leu Arg Ile Phe Phe Ile Arg Ile Ala Arg Leu Leu
1               5                   10                  15

Arg Ile Phe

<210> SEQ ID NO 49
<211> LENGTH: 20
<212> TYPE: PRT
<213> ORGANISM: Artificial Sequence
<220> FEATURE:
<223> OTHER INFORMATION: Synthesized Ctryamp polypeptide

<400> SEQUENCE: 49

Arg Ile Ala Arg Leu Leu Arg Ile Phe Phe Ile Arg Ile Ala Arg Leu
1               5                   10                  15

Leu Arg Ile Phe
            20

<210> SEQ ID NO 50
<211> LENGTH: 21
<212> TYPE: PRT
<213> ORGANISM: Artificial Sequence
<220> FEATURE:
<223> OTHER INFORMATION: Synthesized Ctryamp polypeptide

<400> SEQUENCE: 50

Ile Arg Ile Ala Arg Leu Leu Arg Ile Phe Phe Ile Arg Ile Ala Arg
1               5                   10                  15
```

Leu Leu Arg Ile Phe
            20

<210> SEQ ID NO 51
<211> LENGTH: 22
<212> TYPE: PRT
<213> ORGANISM: Artificial Sequence
<220> FEATURE:
<223> OTHER INFORMATION: Synthesized Ctryamp polypeptide

<400> SEQUENCE: 51

Phe Ile Arg Ile Ala Arg Leu Leu Arg Ile Phe Phe Ile Arg Ile Ala
1               5                   10                  15

Arg Leu Leu Arg Ile Phe
            20

<210> SEQ ID NO 52
<211> LENGTH: 11
<212> TYPE: PRT
<213> ORGANISM: Artificial Sequence
<220> FEATURE:
<223> OTHER INFORMATION: Synthesized Ctryamp polypeptide
<220> FEATURE:
<221> NAME/KEY: MOD_RES
<222> LOCATION: (1)..(1)
<223> OTHER INFORMATION: Xaa(1)=Ac-Phe

<400> SEQUENCE: 52

Xaa Ile Arg Ile Ala Arg Leu Leu Arg Ile Phe
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Synthesized Ctryamp polypeptide

<400> SEQUENCE: 53

Phe Ile Arg Ile Arg Leu Leu Arg Ile Phe
1               5                   10

<210> SEQ ID NO 54
<211> LENGTH: 9
<212> TYPE: PRT
<213> ORGANISM: Artificial Sequence
<220> FEATURE:
<223> OTHER INFORMATION: Synthesized Ctryamp polypeptide

<400> SEQUENCE: 54

Phe Ile Arg Ile Arg Leu Arg Ile Phe
1               5

<210> SEQ ID NO 55
<211> LENGTH: 11
<212> TYPE: PRT
<213> ORGANISM: Chaerilus tryznai Kovarik

<400> SEQUENCE: 55

Phe Ile Arg Ile Ala Arg Leu Leu Arg Ile Phe
1               5                   10

<210> SEQ ID NO 56
<211> LENGTH: 11
<212> TYPE: PRT
<213> ORGANISM: Chaerilus tryznai Kovarik

```
<400> SEQUENCE: 56

Phe Ile Lys Ile Ala Arg Leu Leu Arg Ile Phe
1               5                   10

<210> SEQ ID NO 57
<211> LENGTH: 11
<212> TYPE: PRT
<213> ORGANISM: Chaerilus tryznai Kovarik

<400> SEQUENCE: 57

Phe Ile Arg Ile Ala Lys Leu Leu Arg Ile Phe
1               5                   10

<210> SEQ ID NO 58
<211> LENGTH: 11
<212> TYPE: PRT
<213> ORGANISM: Chaerilus tryznai Kovarik

<400> SEQUENCE: 58

Phe Ile Arg Ile Ala Arg Leu Leu Lys Ile Phe
1               5                   10

<210> SEQ ID NO 59
<211> LENGTH: 11
<212> TYPE: PRT
<213> ORGANISM: Chaerilus tryznai Kovarik

<400> SEQUENCE: 59

Phe Ile His Ile Ala Arg Leu Leu Arg Ile Phe
1               5                   10

<210> SEQ ID NO 60
<211> LENGTH: 11
<212> TYPE: PRT
<213> ORGANISM: Chaerilus tryznai Kovarik

<400> SEQUENCE: 60

Phe Ile Arg Ile Ala His Leu Leu Arg Ile Phe
1               5                   10

<210> SEQ ID NO 61
<211> LENGTH: 11
<212> TYPE: PRT
<213> ORGANISM: Chaerilus tryznai Kovarik

<400> SEQUENCE: 61

Phe Ile Arg Ile Ala Arg Leu Leu His Ile Phe
1               5                   10

<210> SEQ ID NO 62
<211> LENGTH: 11
<212> TYPE: PRT
<213> ORGANISM: Chaerilus tryznai Kovarik

<400> SEQUENCE: 62

Phe Ile Lys Ile Ala Lys Leu Leu Arg Ile Phe
1               5                   10

<210> SEQ ID NO 63
<211> LENGTH: 11
<212> TYPE: PRT
<213> ORGANISM: Chaerilus tryznai Kovarik

<400> SEQUENCE: 63
```

```
Phe Ile Lys Ile Ala Arg Leu Leu Lys Ile Phe
1               5                   10
```

<210> SEQ ID NO 64
<211> LENGTH: 11
<212> TYPE: PRT
<213> ORGANISM: Chaerilus tryznai Kovarik

<400> SEQUENCE: 64

```
Phe Ile Arg Ile Ala Lys Leu Leu Lys Ile Phe
1               5                   10
```

<210> SEQ ID NO 65
<211> LENGTH: 11
<212> TYPE: PRT
<213> ORGANISM: Chaerilus tryznai Kovarik

<400> SEQUENCE: 65

```
Phe Ile Lys Ile Ala Lys Leu Leu Lys Ile Phe
1               5                   10
```

<210> SEQ ID NO 66
<211> LENGTH: 11
<212> TYPE: PRT
<213> ORGANISM: Chaerilus tryznai Kovarik

<400> SEQUENCE: 66

```
Phe Ile His Ile Ala His Leu Leu Arg Ile Phe
1               5                   10
```

<210> SEQ ID NO 67
<211> LENGTH: 11
<212> TYPE: PRT
<213> ORGANISM: Chaerilus tryznai Kovarik

<400> SEQUENCE: 67

```
Phe Ile His Ile Ala Arg Leu Leu His Ile Phe
1               5                   10
```

<210> SEQ ID NO 68
<211> LENGTH: 11
<212> TYPE: PRT
<213> ORGANISM: Chaerilus tryznai Kovarik

<400> SEQUENCE: 68

```
Phe Ile His Ile Ala Lys Leu Leu Arg Ile Phe
1               5                   10
```

<210> SEQ ID NO 69
<211> LENGTH: 11
<212> TYPE: PRT
<213> ORGANISM: Chaerilus tryznai Kovarik

<400> SEQUENCE: 69

```
Phe Ile Arg Ile Ala Lys Leu Leu His Ile Phe
1               5                   10
```

<210> SEQ ID NO 70
<211> LENGTH: 16
<212> TYPE: DNA
<213> ORGANISM: artificial sequence
<220> FEATURE:
<223> OTHER INFORMATION: primer

<400> SEQUENCE: 70

```
tcgacccacg cgtccg                                                    16

<210> SEQ ID NO 71
<211> LENGTH: 13
<212> TYPE: DNA
<213> ORGANISM: artificial sequence
<220> FEATURE:
<223> OTHER INFORMATION: primer

<400> SEQUENCE: 71
gagcggccgc cct                                                       13
```